US009492086B2

(12) United States Patent
Ewers et al.

(10) Patent No.: US 9,492,086 B2
(45) Date of Patent: Nov. 15, 2016

(54) APPARATUS, SYSTEMS, AND METHODS FOR TREATING OBSTRUCTIVE SLEEP APNEA

(71) Applicants: Richard Ewers, Fulterton, CA (US); Kevin Chen, Palos Verdes Estates, CA (US); Andrew Dominguez, San Clemente, CA (US)

(72) Inventors: Richard Ewers, Fulterton, CA (US); Kevin Chen, Palos Verdes Estates, CA (US); Andrew Dominguez, San Clemente, CA (US)

(73) Assignee: Fresca Medical, Inc., San Clemente, CA (US)

( * ) Notice: Subject to any disclaimer, the term of this patent is extended or adjusted under 35 U.S.C. 154(b) by 0 days.

(21) Appl. No.: 14/930,284

(22) Filed: Nov. 2, 2015

(65) Prior Publication Data
US 2016/0051791 A1 Feb. 25, 2016

Related U.S. Application Data

(63) Continuation-in-part of application No. 13/860,926, filed on Apr. 11, 2013, now Pat. No. 9,333,318, and a continuation-in-part of application No. 14/278,587, filed on May 15, 2014.
(Continued)

(51) Int. Cl.
*A61M 16/06* (2006.01)
*A61M 16/20* (2006.01)
(Continued)

(52) U.S. Cl.
CPC ........... *A61B 5/0002* (2013.01); *A61B 5/4809* (2013.01); *A61M 16/0057* (2013.01);
(Continued)

(58) Field of Classification Search
CPC .................... A61M 16/0051; A61M 16/0057; A61M 16/0066; A61M 16/06; A61M 16/0666; A61M 16/0683; A61M 16/20; A61M 16/205; A61M 2016/0027; A61M 2205/3334; A61M 2205/50; A61M 2206/10; A61M 2210/0618; A61M 2230/005; A61M 2230/40
USPC ............ 128/204.18, 204.23, 205.24, 205.25, 128/207.18
See application file for complete search history.

(56) References Cited

U.S. PATENT DOCUMENTS

| 4,655,213 A | 4/1987 | Rapoport |
| 4,823,828 A | 4/1989 | McGinnis |

(Continued)

FOREIGN PATENT DOCUMENTS

| EP | 1893267 A1 | 11/2011 |
| EP | 2287471 B1 | 6/2012 |

(Continued)

OTHER PUBLICATIONS

International Search Report issued Nov. 18, 2014 in PCT/US2014/038215 (6 pages).
(Continued)

*Primary Examiner* — Annette Dixon
(74) *Attorney, Agent, or Firm* — Manuel de la Cerra

(57) ABSTRACT

Apparatus, systems, and methods are provided for treating obstructive sleep apnea. A unitary valve assembly removably located inside the exterior profile of a nasal pillow mask uses positive airway pressure from a low-flow hose to automatically create an on-demand therapeutic air splint in the pharynx. During inspiration the mask's valving system allows room air to be inspired. During exhalation another valve governs therapeutic backpressure equal to the prescribed pressure setting of the CPAP blower machine. The mask may be worn when the CPAP blower machine is off, and systems are provided for turning the CPAP blower machine on only when needed.

23 Claims, 15 Drawing Sheets

Related U.S. Application Data

(60) Provisional application No. 62/239,146, filed on Oct. 8, 2015, provisional application No. 62/184,787, filed on Jun. 25, 2015, provisional application No. 62/163,601, filed on May 19, 2015, provisional application No. 61/613,855, filed on Mar. 21, 2012, provisional application No. 61/775,430, filed on Mar. 8, 2013, provisional application No. 61/838,191, filed on Jun. 21, 2013, provisional application No. 61/962,501, filed on Nov. 8, 2013, provisional application No. 61/909,956, filed on Nov. 27, 2013, provisional application No. 61/927,355, filed on Jan. 14, 2014, provisional application No. 61/823,553, filed on May 15, 2013, provisional application No. 62/134,506, filed on Mar. 17, 2015, provisional application No. 62/246,339, filed on Oct. 26, 2015, provisional application No. 62/246,489, filed on Oct. 26, 2015, provisional application No. 62/246,328, filed on Oct. 26, 2015, provisional application No. 62/246,477, filed on Oct. 26, 2015.

(51) Int. Cl.
*A61B 5/00* (2006.01)
*A61M 16/00* (2006.01)
*A61M 16/08* (2006.01)

(52) U.S. Cl.
CPC ......... *A61M16/06* (2013.01); *A61M 16/0666* (2013.01); *A61M 16/0875* (2013.01); *A61M 16/206* (2014.02); *A61M 16/208* (2013.01); *A61M 16/0069* (2014.02); *A61M 2205/128* (2013.01); *A61M 2205/3569* (2013.01); *A61M 2205/3592* (2013.01); *A61M 2205/50* (2013.01); *A61M 2230/63* (2013.01)

(56) References Cited

U.S. PATENT DOCUMENTS

| | | | |
|---|---|---|---|
| 5,065,756 A | 11/1991 | Rapoport | |
| 5,280,791 A | 1/1994 | Lavie | |
| 5,301,689 A | 4/1994 | Wennerholm | |
| 5,503,146 A * | 4/1996 | Froehlich | A61M 16/0051 128/202.22 |
| 5,567,127 A | 10/1996 | Wentz | |
| 5,649,533 A | 7/1997 | Oren | |
| 5,732,696 A | 3/1998 | Rapoport | |
| 5,881,718 A | 3/1999 | Mortensen et al. | |
| 6,123,071 A | 9/2000 | Berthon-Jones | |
| 6,182,657 B1 | 2/2001 | Brydon | |
| 6,349,724 B1 * | 2/2002 | Burton | A61M 16/0057 128/204.18 |
| 6,526,974 B1 | 3/2003 | Brydon | |
| 6,561,190 B1 | 5/2003 | Kwok | |
| 6,561,191 B1 | 5/2003 | Kwok | |
| 6,581,594 B1 | 6/2003 | Drew | |
| 6,581,601 B2 | 6/2003 | Ziaee | |
| 6,595,212 B1 | 7/2003 | Arnott | |
| 6,662,803 B2 | 12/2003 | Gradon et al. | |
| 6,691,707 B1 | 2/2004 | Gunaratnam | |
| 6,752,150 B1 | 6/2004 | Remmers | |
| 6,823,865 B2 | 11/2004 | Drew | |
| 6,923,181 B2 | 8/2005 | Tuck | |
| 7,011,090 B2 | 3/2006 | Drew | |
| 7,063,086 B2 | 6/2006 | Shahbazpour et al. | |
| 7,066,174 B1 | 6/2006 | Smith et al. | |
| 7,066,178 B2 | 6/2006 | Gunaratnam | |
| 7,159,587 B2 | 1/2007 | Drew | |
| 7,207,335 B2 | 4/2007 | Kwok | |
| 7,341,060 B2 | 3/2008 | Ging | |
| 7,520,277 B1 | 4/2009 | Grady | |
| 7,523,753 B2 | 4/2009 | Gunaratnam | |
| 7,527,055 B2 | 5/2009 | McAuliffe | |
| 7,597,100 B2 | 10/2009 | Ging | |
| 7,735,491 B2 | 6/2010 | Doshi et al. | |
| 7,735,492 B2 | 6/2010 | Doshi | |
| 7,798,148 B2 | 9/2010 | Doshi | |
| 7,845,354 B2 | 12/2010 | Kwok | |
| 7,856,979 B2 | 12/2010 | Doshi | |
| 7,874,291 B2 | 1/2011 | Ging | |
| 7,926,487 B2 | 4/2011 | Drew | |
| 7,934,501 B2 | 5/2011 | Fu | |
| 7,942,150 B2 | 5/2011 | Guney | |
| 7,967,013 B2 | 6/2011 | Ging | |
| 7,992,564 B2 | 8/2011 | Doshi | |
| 8,011,369 B2 | 9/2011 | Gunaratnam | |
| 8,025,055 B1 | 9/2011 | Grady | |
| 8,061,357 B2 | 11/2011 | Pierce | |
| 8,074,646 B2 | 12/2011 | Daly | |
| 8,122,884 B2 | 2/2012 | Daly | |
| 8,122,886 B2 | 2/2012 | Kwok | |
| 8,136,524 B2 | 3/2012 | Ging | |
| 8,210,182 B2 | 7/2012 | Duquette et al. | |
| 8,215,308 B2 | 7/2012 | Doshi | |
| 8,235,046 B2 | 8/2012 | Doshi | |
| 8,240,309 B2 | 8/2012 | Doshi | |
| 8,286,636 B2 | 10/2012 | Gunaratnam | |
| 8,291,909 B2 | 10/2012 | Doshi et al. | |
| 8,297,285 B2 | 10/2012 | Henry et al. | |
| 8,302,606 B2 | 11/2012 | Doshi et al. | |
| 8,337,145 B2 | 12/2012 | Frater | |
| 8,365,736 B2 | 2/2013 | Doshi et al. | |
| 8,371,300 B2 | 2/2013 | Rapoport | |
| 8,371,304 B2 | 2/2013 | Duquette et al. | |
| 8,397,727 B2 | 3/2013 | Ng | |
| 8,402,972 B2 | 3/2013 | Lang | |
| 8,439,039 B2 | 5/2013 | Gunaratnam | |
| 8,573,201 B2 | 11/2013 | Rummery et al. | |
| 8,839,791 B2 | 9/2014 | Allum et al. | |
| 8,844,529 B2 | 9/2014 | Selvarajan et al. | |
| 8,844,531 B2 | 9/2014 | Witt et al. | |
| 8,844,533 B2 | 9/2014 | Allum et al. | |
| 9,027,553 B2 | 5/2015 | Witt et al. | |
| 9,072,855 B2 | 7/2015 | McAuley et al. | |
| 9,132,250 B2 | 9/2015 | Allum et al. | |
| 9,138,555 B2 | 9/2015 | McAuley et al. | |
| 9,144,658 B2 | 9/2015 | Li et al. | |
| 2003/0127096 A1 | 7/2003 | McAuliffe | |
| 2006/0150978 A1 | 7/2006 | Doshi | |
| 2006/0184056 A1 | 8/2006 | De Chazal | |
| 2009/0065729 A1 | 3/2009 | Worboys | |
| 2009/0131803 A1 | 5/2009 | Heneghan | |
| 2009/0133700 A1 | 5/2009 | Martin | |
| 2009/0194109 A1 | 8/2009 | Doshi | |
| 2010/0252041 A1 | 10/2010 | Kapust et al. | |
| 2011/0011400 A1 | 1/2011 | Gentner | |
| 2011/0124979 A1 | 5/2011 | Heneghan | |
| 2011/0155133 A1 | 6/2011 | Barnes et al. | |
| 2011/0253147 A1 | 10/2011 | Gusky et al. | |
| 2011/0259331 A1 * | 10/2011 | Witt | A61M 16/0666 128/204.18 |
| 2011/0259340 A1 * | 10/2011 | Witt | A61M 16/0666 128/207.18 |
| 2012/0111331 A1 | 5/2012 | Witt et al. | |
| 2012/0227742 A1 | 9/2012 | Witt et al. | |
| 2012/0234323 A1 | 9/2012 | Connor | |
| 2012/0325205 A1 | 12/2012 | Allum | |
| 2012/0325211 A1 | 12/2012 | Allum | |
| 2012/0325218 A1 | 12/2012 | Brambilla | |
| 2012/0330183 A1 | 12/2012 | Allum | |
| 2013/0133656 A1 | 5/2013 | Nightingale et al. | |
| 2013/0184602 A1 | 7/2013 | Brambilla | |
| 2013/0186394 A1 | 7/2013 | Hallett | |
| 2013/0255684 A2 | 10/2013 | Allum et al. | |
| 2014/0053846 A1 | 2/2014 | Wood | |
| 2014/0088373 A1 | 3/2014 | Phillips | |
| 2014/0200474 A1 | 7/2014 | Selvaraj | |
| 2014/0246025 A1 | 9/2014 | Cragg et al. | |
| 2014/0278229 A1 | 9/2014 | Hong | |
| 2014/0281547 A1 | 9/2014 | Modzelewski | |

(56) References Cited

U.S. PATENT DOCUMENTS

| | | | |
|---|---|---|---|
| 2015/0034079 A1 | 2/2015 | Allum et al. | |
| 2015/0040907 A1 | 2/2015 | Hakim | |
| 2015/0128948 A1 | 5/2015 | Rapoport | |

FOREIGN PATENT DOCUMENTS

| | | | |
|---|---|---|---|
| EP | 2530327 | A2 | 12/2012 |
| GB | 2021421 | A | 12/1979 |
| WO | 9741812 | A1 | 11/1997 |
| WO | 0132251 | A1 | 5/2001 |
| WO | 0215969 | A2 | 2/2002 |
| WO | 2004112606 | A1 | 12/2004 |
| WO | 2007143535 | A2 | 12/2007 |
| WO | 2009089807 | A1 | 7/2009 |
| WO | 2012048364 | A1 | 4/2012 |

OTHER PUBLICATIONS

CPAP Systems and Accessories: Comfort Accuracy and High Flows. Vital Signs, Inc. General Electric Healthcare Company. 2009, 2 pages.
Deegan, P., et al. Effects of positive airway pressure on upper airway dilator muscle activity and ventilatory timing. Journal of Applied Physiol. Jul. 1996; 81 (1 ): 470-4.
Duncan, A., et al. PEEP and CPAP. Anaesth Intensive Care. Aug. 1986; 14(3): 236-50.
Garrard, C., et al. The effects of expiratory positive airway pressure on functional residual capacity in normal subjects. Grit Care Med. Sep.-Oct. 1978; 6(5): 320-2.
Gillick, JS. Spontaneous positive end-expiratory pressure (sPEEP). Anesthesia & Analgesia. Sep.-Oct. 1977; 56(5): 627-32. PubMed PMID: 333990.
Heinzer R, et al. Effect of expiratory positive airway pressure on sleep disordered breathing. Sleep. Mar. 2008; 31 (3): 429-32.
Juhasz, J. et al. Proportional positive airway pressure: a new concept to treat obstructive sleep apnoea. European Respiratory Journal. 2001; 17: 467-473.
Layon, J., et al. Continuous positive airway pressure and expiratory positive airway pressure increase functional residual capacity equivalently. Chest. Apr. 1986;89(4):517-21.
Resta, 0., et al. The role of the expiratory phase in obstructive sleep apnoea. Respir Med. Mar. 1999;93(3):190-5.
Sanders, M., et al. Obstructive sleep apnea treated by independently adjusted inspiratory and expiratory positive airway pressures via nasal mask. Physiologic and clinical implications. Chest. Aug. 1990; 98(2): 317-24.
Schlobohm, R., et al. Lung volumes, mechanics, and oxygenation during spontaneous positivepressure ventilation: the advantage of CPAP over EPAP. Anesthesiology. Oct. 1981;55(4):416-22.
Schmidt, G., et al. EPAP without intubation. Grit Care Med. Jui-Aug. 1977; 5(4): 207-9.
Series, F., et al. Changes in upper airway resistance with lung inflation and positive airway pressure. American Physiological Society. Mar. 1990; 68(3): 1075-107.
Sturgeon, C. Jr, et al. PEEP and CPAP: cardiopulmonary effects during spontaneous ventilation. Anesth Analg. Sep.-Oct. 1977; 56(5):633-41. PubMed PMID: 20822.
Tummons, J. A positive end-expiratory pressure-nasal-assist device (PEEP-NAD) for treatment of respiratory distress syndrome. Anesthesiology. Jun. 1973; 38(6):592-5.
Search Report and Written Opinion issued in PCT/US13/36246 mailed Sep. 6, 2013 (19 pages).
U.S. Appl. No. 29/448,107, filed Mar. 8, 2013 Gordon et al.
U.S. Appl. No. 29/461,138, filed Jul. 18, 2013 Chen et al.
U.S. Appl. No. 29/461,144, filed Jul. 18, 2013 Chen et al.
U.S. Appl. No. 29/461,143, filed Jul. 18, 2013 Chen et al.
U.S. Appl. No. 29/464,533, filed Aug. 16, 2013 Chen et al.
U.S. Appl. No. 29/465,007, filed Aug. 22, 2013 Chen et al.
International Search Report and Written Opinion issued Jun. 24, 2016 in PCT/US2016/023798 (9 pages).

* cited by examiner

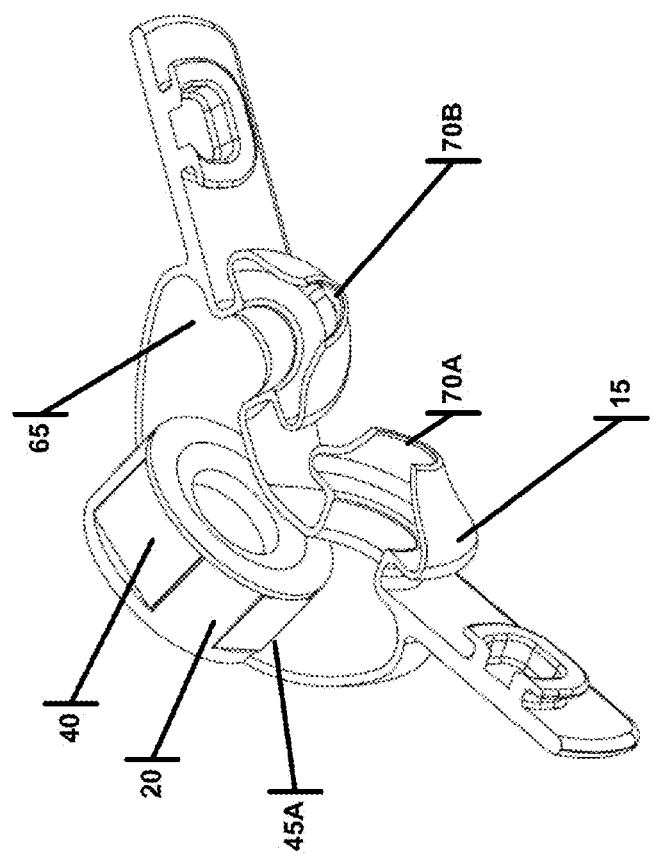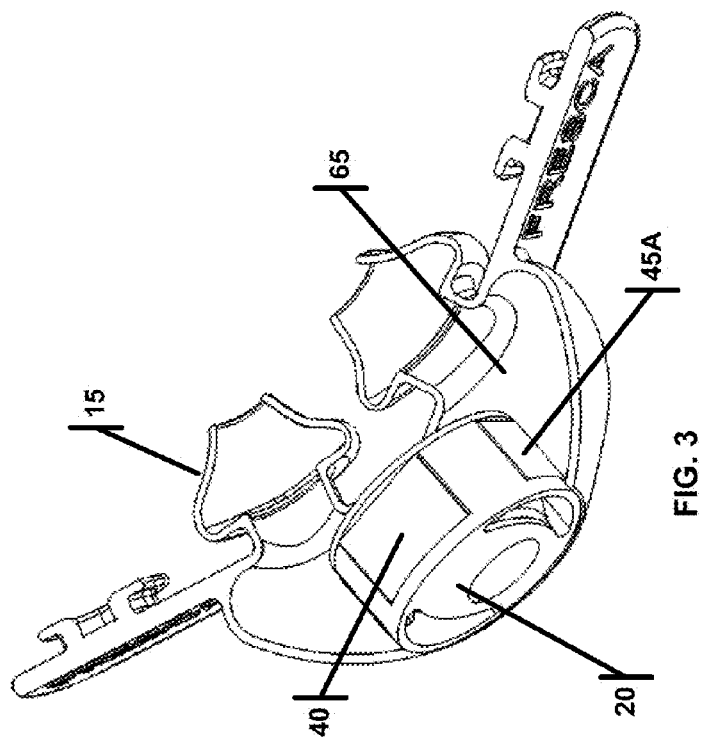

Inhale

Exhale

Apnea

Inhale (w/o positive pressure)

Exhale (w/o positive pressure)

(Pressure set at 10 cm/H2O)

(Pressure set at 10 cm/H2O)

(Pressure set at 10 cm/H2O)

(Pressure set at 10 cm/H2O)

APPARATUS, SYSTEMS, AND METHODS FOR TREATING OBSTRUCTIVE SLEEP APNEA

1.0 TECHNICAL FIELD

The present invention is related to medical systems, devices, and methods. More specifically, the invention is related to systems, devices and methods for treating obstructive sleep apnea or snoring.

2.0 BACKGROUND

Obstructive sleep apnea (OSA) is a common medical disorder that can be quite serious. It has been reported that approximately one in twenty-two Americans (about 12,000,000 people) suffer from OSA, and many cases go undiagnosed. Chronic fatigue has long been recognized as the hallmark of OSA, but more recently, large clinical studies have shown a strong link between OSA, strokes and death.

Obstructive sleep apnea is a condition in which the flow of air pauses or decreases during breathing while one is asleep, because the airway has become narrowed, blocked, or floppy. (See FIG. 1A of published patent application US20140246025 A1 to Cragg et al., published Sep. 4, 2014, which is incorporated herein by reference, illustrating an airway A during normal breathing and FIG. 1B therein illustrating the airway A during OSA.) A pause in breathing is called an apnea episode, while a decrease in airflow during breathing is called a hypopnea episode. Almost everyone has brief apnea or hypopnea episodes while they sleep. In OSA, however, apnea episodes occur more frequently and last longer than in the general population. OSA has become an increasingly costly medical condition in recent years, as the disorder is more prevalent in obese people and obesity has become significantly more prevalent. Unfortunately, the currently available options for treating OSA are not ideal.

A person with OSA usually begins snoring heavily soon after falling asleep. Often the snoring gets louder. The snoring is then interrupted by a long silent period during which there is no breathing. This is followed by a loud snort and gasp, as the person attempts to breathe. This pattern repeats. Many people wake up unrefreshed in the morning and feel sleepy or drowsy throughout the day. This is called excessive daytime sleepiness (EDS). People with sleep apnea may act grumpy or irritable, be forgetful, fall asleep while working, reading, or watching TV, feel sleepy or even fall asleep while driving, or have hard-to-treat headaches. OSA sufferers may also experience depression that becomes worse, hyperactive behavior (especially in children), or leg swelling (if severe).

The most widely used therapy for OSA is Continuous Positive Airway Pressure (CPAP). As shown in FIG. 2 of US20140246025 A1 to Cragg et al., a CPAP system 10 typically consists of a mask 1a-12c fitting in or over the nose or nose and mouth, an air pressurizing console 14, and a tube 16 connecting the two (typically a six-foot long hose with a 20 mm diameter bore). CPAP works by pressurizing the upper airway throughout the breathing cycle, essentially inflating the airway to keep it open and thus creating what is sometimes referred to as a "pneumatic splint." This flow is set at a pressure that has been predetermined through medical testing to be appropriate to create a pneumatic splint in the user's airway. This prevents airway collapse and allows the user to breath without obstruction. Because the masks 12a-12c typically leak air, CPAP systems have to provide an airflow rate of up to 200 liters per minute (approximate figure based on unpublished data). The high airflow rate is needed for multiple reasons. First, all the air needed for breathing must come through the hose. Second, conventional masks have an intended leak built in for the purpose of constant "CO2 washout." Third, these systems achieve the required pressure by using a high airflow rate to generate a back-pressure at the mask end where the air is leaking out. Unfortunately, this high flow rate makes breathing feel quite uncomfortable for many users and requires a relatively large, noisy pressurizing console 14. Additionally, the high required flow rates of CPAP often cause discomfort during exhalation due to increased resistance, as well as nasal dryness, dry mouth, ear pain, rhinitis, abdominal bloating and headaches.

The overwhelming shortcoming of CPAP is poor user compliance. Over half of all users who try CPAP stop using it. Users dislike the side effects mentioned above, as well as having to wear an uncomfortable, claustrophobic mask, being tethered to a pressurizing console, the noise of the console, traveling with a bulky device, and a loss of personal space in bed.

Many CPAP devices and alternatives to CPAP have been developed, but all have significant shortcomings. Less invasive attempts at OSA treatment, such as behavior modification, sleep positioning and removable splints to be worn in the mouth, rarely work. A number of different surgical approaches for treating OSA have also been tried, some of which are still in use. For example, Uvulopalatopharyngoplasty (UPPP) and Laser Assisted Uvula Palatoplasty (LAUP) are currently used. Surgical approaches, however, are often quite invasive and not always effective at treating OSA.

One alternative approach to OSA treatment is to provide a pneumatic splint during the expiratory portion of the respiratory cycle by producing a partial blockage in the nose or mouth, thus slowing the release of air during expiration and increasing positive pressure in the airway. The simplest way to form an expiratory pneumatic splint, pursing the lips, has been shown to open the upper airway and improve breathing in emphysema users. This type of maneuver is generically labeled Expiratory Positive Airway Pressure (EPAP).

Ventus Medical, Inc. (http://www.proventtherapy.com/ventus_medical) has developed a removable nasal EPAP device to produce such a pneumatic splint during exhalation (the Provent® Sleep Apnea Therapy). (See, for example, published patent application US20060150978 A1 to Doshi et al., published Jul. 13, 2006, which is incorporated herein by reference.) This device restricts exhalation by forcing expired air through several small orifices attached to the nose. This is labeled a Fixed Orifice Resistor (FOR). Shortcomings of this therapy are that 1) the fixed hole exhalation valve does not have a capped maximum pressure, 2) the pressure increases immediately upon exhalation and therefore makes it difficult to exhale, and 3) with no assistance of additional pressure from an external source, if the user has an apneic event there is no 'rescue pressure'—i.e., the flow supplied by the blower box. A further disadvantage is that the Provent® device or any FOR restricts expiratory airflow using a fixed hole for resistance. This leads to an uncomfortable spike in nasal pressure at the beginning of expiration when airflow is highest and a less efficacious decrease in nasal pressure at the end of expiration when airflow is lowest. Another shortcoming of the Provent® device is that it produces the pneumatic splint only during exhalation—i.e., there is no increased pressure during inhalation.

In addition, the device is not effective in mouth breathers or users who become mouth breathers when resistance is added to the nasal passages. Thus, the Provent® device is useful only in moderate cases of OSA that do not convert to mouth breathing.

Although snoring is not as severe a condition as OSA, it does affect lives adversely. Snoring can adversely affect sleep quality and can make sleeping with a spouse or other partner difficult. Although many snoring therapies have been tried, including Breathe Right® Nasal Strips and more invasive approaches in more severe cases, no ideal solution has been found.

Therefore, it would be advantageous to have improved systems, devices and methods for treating OSA and snoring. Ideally, such systems, devices and methods would be less cumbersome than currently available CPAP systems, to improve user compliance. Also ideally, such systems, devices and methods would provide some of the advantages of an expiratory pneumatic splint. At least some of these objectives were met by the embodiments described in US20140246025 A1 to Cragg et al., previously incorporated herein by reference (herein sometimes referred to as "Cragg '025").

Cragg '025 utilized a novel system of valves to allow inspiration of air supplied via the hose and also from inlets in the mask that take in room air. In various example embodiments Cragg '025 provided variable resistance to expiratory air flow using a resistive mechanism other than infused external air that increases over the course of expiration, thus providing an easier, more comfortable start to expiration while maintaining airway pressure toward the end of expiration (e.g., by decreasing resistance to expiratory flow when intranasal pressure reaches a threshold pressure and/or by gradually increasing resistance to expiratory air flow until intranasal pressure reaches the threshold pressure). Another improvement in various embodiments of Cragg '025 was that lower air flow rates were used (e.g., less than or equal to 20 L/min), while still supplying the desired therapeutic pressure (e.g., between about 4 cmH20 and 20 cmH20), thus requiring less power and smaller device components than traditional CPAP and reducing side effects. Still another improvement of Cragg '025 was a less cumbersome, more form-fitting mask that reduced air leaks and was more comfortable to wear than prior CPAP masks and eliminated the need for high flow rates because there was no need to compensate for air leaks. Accordingly, the devices described therein could be used in connection with a small diameter hose (e.g., having a diameter of less than or equal to about 15 mm), thus decreasing the bulkiness of the system.

While Cragg '025 was an important improvement over the state of the art, it required and relied upon a special system of protruding valves that had to be pre-adjusted or set to suit each user. It would be advantageous to improve upon the system of Cragg '025 by making the system simpler and more compact in design, simpler to use, and more robust.

3.0 SUMMARY

Provided in various example embodiments is an improved apparatus, system, and method for treating obstructive sleep apnea comprising a dynamically-responding "smart valve" that can create exhalation pressure equivalent to the pressure of the supplied air. A version of this smart valve may utilize a channel to supply pressurized air for breathing with a parallel channel that provides a pressure to control the resistance of the valve. In these embodiments the two channels may use the same source air at the same source pressure. Also in various example embodiments, the supplied air and the valve controlling air may be combined into a single hose with a single lumen. This has unique advantages, in that the hose can be smaller, more supple (an important user feature is not having a cumbersome hose to distract from sleeping), easier to clean (the system need not have any elongated, small lumens that end in a closed compartment in the valve resistance generating chamber), and easier to connect as only a single orientation independent hub is needed at either end. Additionally, in various example embodiments the system may comprise a one-way flapper in line with the airflow adapted to prevent "back flow" into the supply tube during exhalation. In various example embodiments, such a system may comprise discrete valves for inspiration and a discrete valve for exhalation.

Also provided in various example embodiments is an exhalation valve that incorporates at least partially the inspiratory flow path and valves. When considering the mask and its need for communication to the atmosphere, it was observed that the inspiratory valves need to communicate with the ambient atmosphere of the room, while the expiration valve likewise needs to communicate with the room atmosphere. It was recognized that it would be a more efficient and compact design if both of these valves could share a common communication with the room. Accordingly, in various example embodiments, the inspiratory and expiration valves both use the same vent on the mask. This has the benefit of facilitating use of a single valve housing to contain all of the needed valves. With a combined valve assembly, inspiratory valves do not have to be pre-assembled on the mask, which reduces parts and costs, and the user does not have to repeatedly install and uninstall a series of valves for use and cleaning. Thus, various example embodiments may comprise a single and easy-to-install valve canister.

Another feature provided in various example embodiments is that all valve opening and closing components may be configured so as to be not visible or accessible to the user during use. In previous designs, these valves and their components were accessible, particularly with regard to inspiratory valves, which typically comprised an orifice and an elastomeric one-way flapper installed on the outward-facing surface of the mask. In these prior embodiments, it was readily possible to tamper with the valve with a finger, paper clip, or the like. But in the present system, all valve flappers and closing membranes may be configured to be not directly accessible, for instance by housing them well within the bore of a crescent-shaped set of slots, for example.

Further provided in various example embodiments is an exhalation valve that does not have a rigid closure component. In certain embodiments the exhalation valve may utilize an inflating, distending, membrane to impinge on a rigid disk that in turn closes the exhalation valve orifice. But in other embodiments the rigid disk may be eliminated. For example, the internal geometry of the exhalation valve may be configured to allow an inflating, distending membrane to directly block the exhalation airflow. This may be important for several reasons. For example, in this type of embodiment there is no hard part to rattle or generate noise due to its movement. Second, there is no need to include a rubber grommet or elastomeric base for the disk to better seal against. Third, the flow path may be simplified for better flow dynamics and easier cleaning Fourth, this type of embodiment may be more robust in that it may be more likely to close securely in the presence of minor debris, such as lint or residue, because the closing component may comprise a morphable soft membrane such as 10 Shore A silicone (a particularly soft membrane material).

Accordingly, provided in various example embodiments is a mask (15) for treating a patient suffering from obstructive sleep apnea, the mask adapted to be connected to an air flow generator (200) and constructed to cover at least the nostrils of the patient, the mask comprising: a cavity (65) in fluid connection with the nostrils of the patient; an inlet pressure port (50) constructed to be attached to the air flow generator; the inlet pressure port fluidly connected to the cavity via an inlet pressure one-way valve (40, 42) that is constructed to allow air flow from the air flow generator to the cavity with little resistance and blocking air flow from the cavity to the air flow generator; the inlet pressure port fluidly connected to an expiration valve (30, 35), wherein the expiration valve is fluidly connected to the cavity and to the outside of the mask, the expiration valve restricts air flow from the cavity to the outside of the mask, wherein the restriction is dependent on the pressure of air in the inlet pressure port (75); and an inspiration one-way valve (45A, B; 47A, B) fluidly connected to the cavity and to the outside of the mask, the inspiration valve is constructed to allow air flow from the outside of the mask into the cavity with little resistance and blocking air flow from the cavity to the outside of the mask.

In various example embodiments the device may further comprise a valve cartridge (20) that comprises the inlet pressure one way valve, the expiration valve and the inspiration one way valve. In various example embodiments the cartridge may be removable. In various example embodiments the inspiration one way valve comprises two valves. In various example embodiments the device may further comprise an ambient pressure port (55A, B), wherein the inspiration one-way valve and the expiration valve are fluidly connected to the ambient port. In various example embodiments the inlet pressure one way valve may comprise a membrane (40) and a valve seat (42). In various example embodiments the inspiration one way valve may comprise a membrane (45A, B) and a valve seat (47A, B). In various example embodiments the expiration valve may comprise a membrane (35) and a valve seat (30). In various example embodiments the shape of the membrane may be dependent on the pressure of air in the inlet pressure port.

Also provided in various example embodiments is a mask (15) for treating a patient suffering from obstructive sleep apnea, the mask adapted to be connected to an air flow generator (200) and constructed to cover at least the nostrils of the patient, the mask comprising: a cavity (65) in fluid connection with the nostrils of the patient; an inlet pressure port (50) constructed to be attached to the air flow generator; the inlet pressure port fluidly connected to the cavity via an inlet pressure one-way valve (40, 42); the inlet pressure port fluidly connected to an expiration valve (30, 35), wherein the expiration valve is fluidly connected to the cavity and to the outside of the mask; an inspiration one-way valve (45A, B; 47A, B) fluidly connected to the cavity and to the outside of the mask; the mask having at least an inspiration mode, a rest/apnea mode and an expiration mode; the inspiration mode occurs when the patient inspires air, during which the inspiration one-way valve and the inlet pressure one-way valve are open; the rest/apnea mode occurs when the patient is neither inspiring air nor expiring air, during which the inlet pressure one-way-valve is open, and the expiration valve and inspiration one-way valve are closed; and the expiration mode occurs when the patient expires air, during which the expiration valve is open and the inlet pressure one-way valve and the inspiration one-way valve are closed.

In various example embodiments the mask may further comprise a disconnected mode when the air flow generator is not providing airflow to the mask: during which when a patient inspires the inspiration one-way valve and/or the expiration valve are open; and during which when a patient expires the inspiration one-way valve is closed and the expiration valve is open.

Further provided in various example embodiments is a system for treating a patient suffering from obstructive sleep apnea, system comprising: an air flow generator (200), which further comprises a controller (210) that adjusts an air flow pressure and volume to be generated; a tube connected to the air flow generator; a mask (15) constructed to cover at least the nostrils of the patient, the mask comprising: a cavity (65) in fluid connection with the nostrils of the patient; an inlet pressure port (50) constructed to be attached to the air flow generator via the tube; the inlet pressure port fluidly connected to the cavity via an inlet pressure one-way valve (40, 42) that is constructed to allow air flow from the air flow generator to the cavity with little resistance and blocking air flow from the cavity to the air flow generator; the inlet pressure port fluidly connected to an expiration valve (30, 35), wherein the expiration valve is fluidly connected to the cavity and to the outside of the mask, the expiration valve restricts air flow from the cavity to the outside of the mask, wherein the restriction is dependent on the pressure of air in the inlet pressure port (75); and an inspiration one-way valve (45A, B; 47A, B) fluidly connected to the cavity and to the outside of the mask, the inspiration valve is constructed to allow air flow from the outside of the mask into the cavity with little resistance and blocking air flow from the cavity to the outside of the mask.

In various example embodiments the controller may comprise a delay circuit (220) that delays the generation of air flow from the air flow generator for a predetermined amount of time. In various example embodiments a predetermined maximum pressure may be set and the air flow generator gradually increases the pressure of air generated until the maximum pressure is reached (180). In various example embodiments the system may further comprise a sleep detector (260) that signals the controller that the patient is asleep, thus activating the generation of air flow from the air flow generator. In various example embodiments the system may further comprise setting a predetermined maximum pressure and the air flow generator gradually increases the pressure of air generated until the maximum pressure is reached. In various example embodiments the system may further comprise the sleep detector being worn by the patient and adapted to take biometric readings of the patient. In various example embodiments the system may further comprise the sleep detector being wirelessly connected to the controller (210). In various example embodiments the system may further comprise the tube consisting of a single lumen connecting the mask to the air flow generator.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

4.0 BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure. It will be understood that certain components and details may not appear in the figures to assist in more clearly describing the invention.

FIG. 2A does not show the inspiration one-way valve membranes 45A, B or the inlet pressure one-way valve membrane 40.

FIG. 2B does not show the inspiration one-way valve membranes 45A, B or the inlet pressure one-way valve membrane 40.

FIG. 3 is a front perspective section view of the example CPAP apparatus of FIG. 1, according to various example embodiments.

FIG. 4 is a rear perspective section view of the example CPAP apparatus of FIG. 1, according to various example embodiments.

5.0 DETAILED DESCRIPTION OF EXAMPLE EMBODIMENTS

Figure 1:
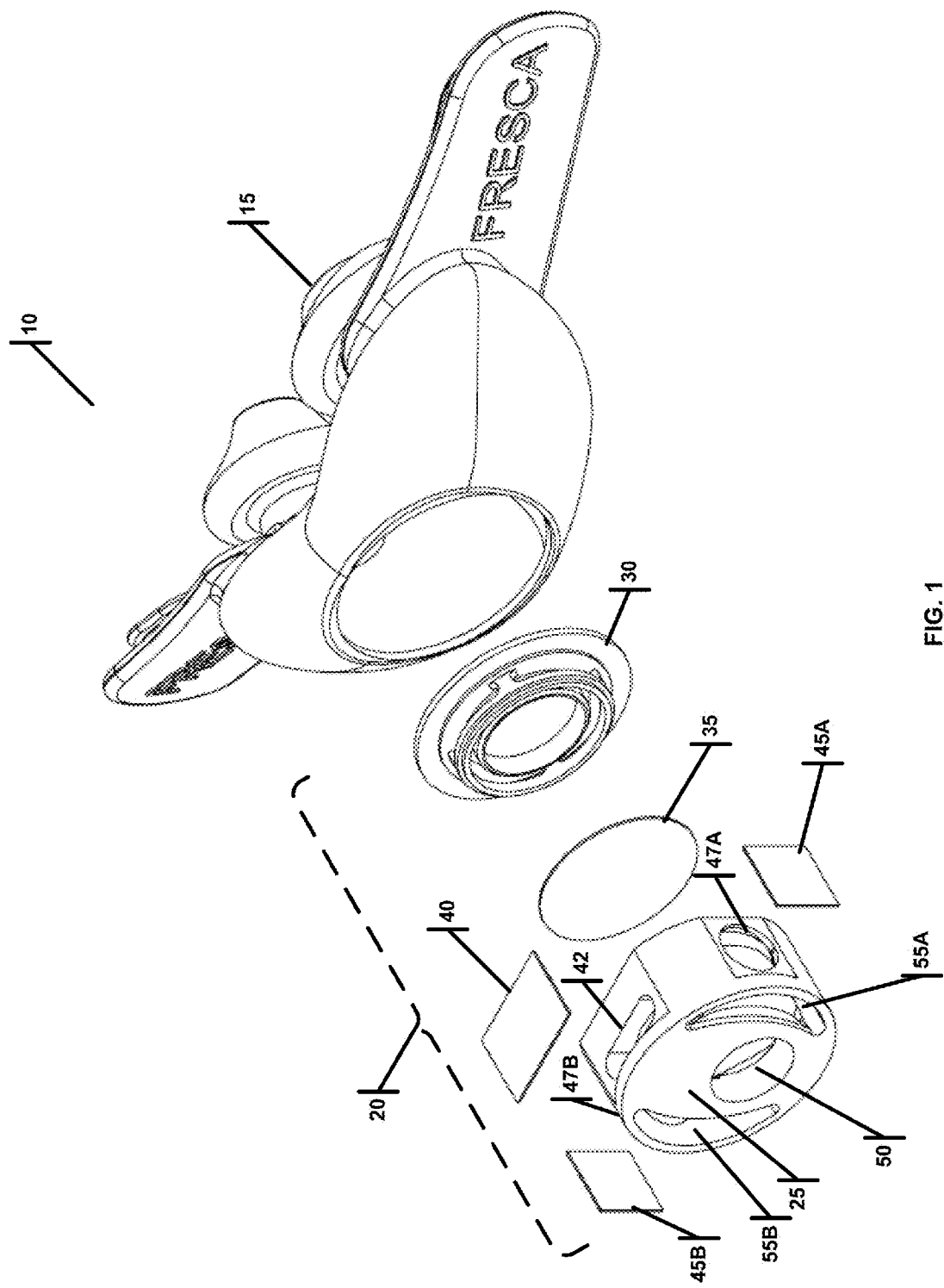
FIG. 1 is an exploded perspective view of an example CPAP apparatus according to various example embodiments.
Figure 2A:
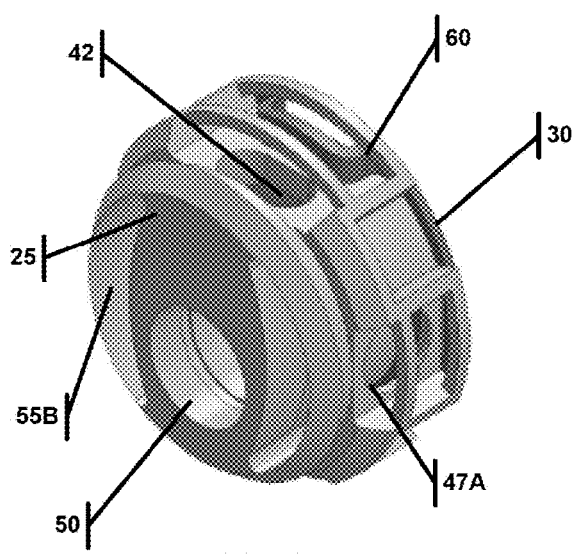
FIG. 2A is a front perspective view of an example valve cartridge adapted for use with the example CPAP apparatus of FIG. 1, according to various example embodiments.
Figure 2B:
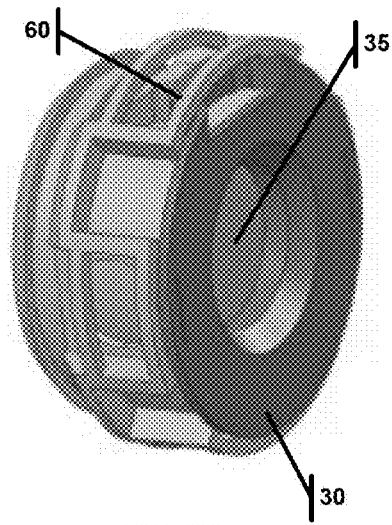
FIG. 2B is a rear perspective view of the example valve cartridge of FIG. 2A according to various example embodiments.
Figure 2C:
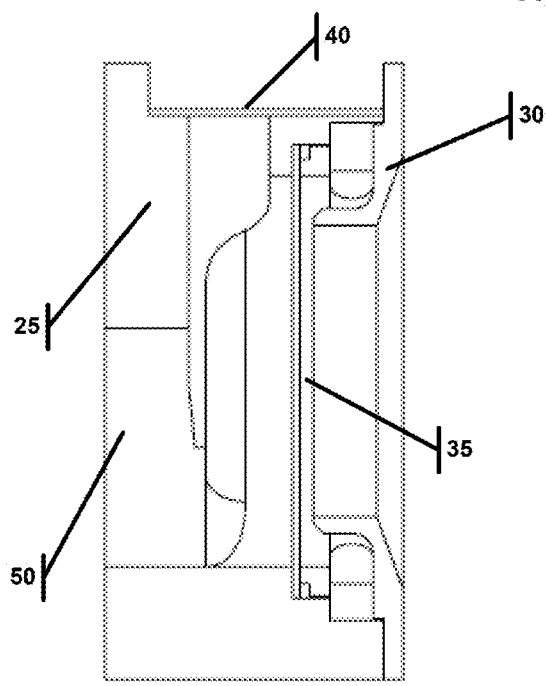
FIG. 2C is a section side view taken through the middle of the example valve cartridge of FIG. 2A according to various example embodiments.

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity.

However, it should be noted that some embodiments include multiple iterations of a technique or multiple mechanisms unless noted otherwise. Similarly, various steps of the methods shown and described herein are not necessarily performed in the order indicated, or performed at all in certain embodiments. Accordingly, some implementations of the methods discussed herein may include more or fewer steps than those shown or described. Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

The following list of example features corresponds with FIGS. 1-17D and is provided for ease of reference, where like reference numerals designate corresponding features throughout the specification and figures:

Sleep Apnea Device 10
  Nasal Pillow/mask 15
  Valve cartridge 20
  Valve body 25
  Expiration Valve Seat 30
  Expiration Valve Membrane 35
  Inlet pressure one-way valve Membrane 40
  Inlet pressure one-way valve seat 42
  Inspiration one-way valve membranes 45A, B
  Inspiration one-way valve seat 47A, B
  Inlet pressure port 50
  Ambient Pressure ports 55A, B
  Valve Body connection structure 60
  Cavity 65
  Compliant/malleable nasal seat 70A, B
  Positive pressure 75
  Inspiration ambient air stream 80
  Inspiration nasal air stream 85
  Inspiration positive pressure air stream 90
  Inspiration cavity pressure 93
  Expiration nasal air stream 95
  Expiration ambient air stream 100
  Expiration positive pressure air stream 105
  Expiration cavity pressure 107
  Apnea positive pressure air stream 110
  Apnea nasal air stream 115
  Apnea cavity pressure 117
  Non-positive pressure inspiration nasal air flow 120
  Non-positive pressure inspiration ambient air flow 130
  Non-positive pressure expiration nasal air flow 140
  Non-positive pressure expiration ambient air flow 150
  Conventional positive operation region 160
  Positive air pressure of zero while user is falling asleep 170
  Increase of positive air pressure after the user falls asleep 180
  Operation region of sleep apnea device 190
  Positive Air Flow Generator 200
  Controller 210
  Delay circuit 220
  Initiation control 240
  Transceiver 250
  Sleep detector 260
  Cavity Pressure 270
  Cavity Pressure supplied by positive air flow generator 280

Some of the inventors of the innovation described herein have also disclosed other masks and structures designed to treat sleep apnea. Those masks and structures are described in U.S. patent application Ser. No. 14/278,587, filed May 15, 2014, titled "Auto-Feedback Valve For A sleep Apnea Device," U.S. patent application Ser. No. 13/860,926, filed Apr. 11, 2013, titled "Sleep Apnea Device," U.S. Provisional Application Ser. No. 61/623,855, filed Apr. 13, 2012, titled "Sleep Apnea Device," U.S. Provisional Application Ser. No. 61/775,430, filed Mar. 8, 2013, titled "Sleep Apnea Device," U.S. Provisional Application No. 61/823,553, filed May 15, 2013, titled "Sleep Apnea Device," U.S. Provisional Application No. 61/838,191, filed Jun. 21, 2013, titled "Sleep Apnea Device," U.S. Provisional Application No. 61/962,501, filed Nov. 8, 2013, titled "Sleep Apnea Device," U.S. Provisional Application No. 61/909,956, filed Nov. 27, 2013, titled "Sleep Apnea Device," U.S. Provisional Application No. 61/927,355, filed Jan. 14, 2014, titled "Valve with Pressure Feedback," U.S. Provisional Application No. 62/134,506 filed Mar. 17, 2015 titled "Valve with Pressure Feedback Draft Provisional Application," U.S. Provisional Application No. 62/163,601, filed May 19, 2015, titled "Airflow Generator with Delayed Onset", U.S. Provisional Application No. 62/184,787 filed Jun. 25, 2015 titled "Sleep Apnea Device," and U.S. Provisional Application No. 62/239,146 filed Oct. 8, 2015 titled "Sleep Apnea Device," U.S. Provisional Application No. 62/246,339 filed Oct. 26, 2015 titled "Venting of a Valved CPAP Mask to Create a Comfortable Breathing Sensation," U.S. Provisional Application No. 62/246,489 filed Oct. 26, 2015 titled "Managing Sleep Apnea with Pulse Oximeters and With Additional Assessment Tools," U.S. Provisional Application No. 62/246,328 filed Oct. 26, 2015 titled "Novel Low Flow Technology Designed to Meet CPAP Efficacy," and U.S. Provisional Application No. 62/246,477 filed Oct. 26, 2015 titled "Composite Construction Air Delivery Hose for use with CPAP Treatment" all of which are assigned to the same assignee as the present application and are also hereby incorporated by reference in their entirety.

Now turning to FIGS. 1 through 10C, provided in various example embodiments is a sleep apnea device or apparatus 10, comprising a unitary nasal pillow/mask 15 configured to be connected to a source of pressurized air, such as a conventional CPAP blower box (not shown) via a small-diameter single-lumen hose (now shown). For example, an outer diameter of the hose can be between about 3.0 mm and about 15.0 mm. In some embodiments, an inner diameter of those hose can be less than or equal to about 10.0 mm, e.g., between about 5.0 mm and about 10.0 mm. In some embodiments, a wall thickness of those hose can be less than or equal to about 1.0 mm, e.g., between about 0.5 mm and about 0.75 mm. The smaller hose is less bulky than traditional hoses for CPAP devices. Such a hose is described in U.S. patent application Ser. No. 14/278,587 filed on May 15, 2014 and 62/246,477 filed on Oct. 26, 2015, the contents of both are incorporated by reference in their entireties. Nasal pillow/mask 15 may be configured to be sealably affixed to the nostrils of a user with compliant/malleable nasal seats 70A, 70B (FIG. 4) and held in place by adjustable headgear (not shown). Nasal pillow/mask 15 may be formed from any appropriate material, such as silicone.

Nasal pillow/mask 15 may be configured to removably receive therein a centrally-located valve cartridge 20, for instance partially or entirely within a sealed internal cavity 65 of nasal pillow/mask 15 (FIGS. 3, 4), such that the valve cartridge is removably located almost entirely or entirely inside the exterior profile of the nasal pillow mask. Valve cartridge 20 may in various example embodiments be a unitary cylindrical assembly comprising a valve body 25 defining an inlet pressure port 50 configured to removably attach with the hose (not shown) communicating pressurized air 90 from the CPAP blower box (not shown). Valve body 25 may further define ambient pressure ports 55A, 55B, which may be crescent-shaped and located adjacent and on opposite sides of the inlet pressure port 50. Ambient pressure ports 55A, 55B may be configured to be in communication with ambient air 80 in the room where the device 10 is being used.

One or more flexible expiration valve membranes 35 (e.g., a distensible or morphable soft membrane, such as a thin sheet of 10 Shore A silicone) may be removably assembled between the valve body 25 and one or more mating expiration valve seats 30, for instance by a valve body connection structure 60 (such as a compression-fit or snap-together mechanism 60), such that, each valve membrane 35 is exposed on one side (distal expiration valve seat 30) to pressurized air 90 communicated through the inlet pressure port 50, and is exposed on the opposite side (proximate expiration valve seat 30) to expiration nasal air stream 95. Expiration valve membranes 35 may be formed from a distensible or morphable soft membrane, such as a thin sheet of 10 Shore A silicone, which creates a quiet, effective, and robust seal that tends to effectuate a seal even in the presence of minor debris, lint, and residue.

Valve body 25 may further comprise one or more inlet pressure one-way valve membranes 40 that in use are exposed on one side to pressurized air 90 communicated through, inlet pressure port 50, and are exposed on the opposite side to expiration nasal air stream 95. One-way valve membranes 40 may be configured to open and allow pressurized air 90 to flow from inlet pressure port 50 into cavity 65 of nasal pillow/mask 15 when pressurized air 90 is at a higher pressure than expiration nasal air stream 95. Conversely, one-way valve membranes 40 may be configured to close and seal against inlet pressure one-way valve seat 42 formed in valve body 25 to prevent air flow between inlet pressure port 50 and cavity 65 when pressurized air 90 is not at a higher pressure than expiration nasal air stream 95.

Valve body 25 may also comprise one or more inspiration one-way valve membranes 45A, 45B, configured such that in use each inspiration one-way valve membrane 45A, 45B is exposed on one side (proximate ambient pressure ports 55A, 55B, respectively) to ambient air 80 communicated through ambient pressure ports 55A, 55B, respectively, and is exposed on the opposite side (distal ambient pressure ports 55A, 55B, respectively) to expiration nasal air stream 95. Inspiration one-way valve membranes 45A, 45B may be configured to open and allow ambient air 80 to flow from ambient pressure ports 55A, 55B, respectively, into cavity 65 of nasal pillow/mask 15 when ambient air 80 is at a higher pressure than expiration nasal air stream 95. Conversely, one-way valve membranes 40 may be configured to close and seal against inspiration one-way valve seats 47A, 47B, formed in valve body 25 to prevent air flow between ambient pressure ports 55A, 55B, and cavity 65 when ambient air 80 is not at a higher pressure than expiration nasal air stream 95. The expiration valve 35 and inspiration valves 45A, 45B, share the same ambient pressure ports 55A, 55B, such that the device is simple to manufacture and easy for the user to clean. Also, the example design shown in the figures includes no dead-end cavities or difficult-to-access recesses in the air flow channels, which allows a user to clean and dry the device effectively without leaving moisture that might breed mold or mildew.

An example sleep apnea device or apparatus 10 will now be described in use as part of a system, according to various example embodiments. The nasal pillow/mask 15 may be connected with a traditional CPAP blower box (not shown) via a hose (not shown). The nasal pillow/mask 15 may be affixed to the nostrils of a user (not shown) via a silicone or similar nasal interface 70A, 70B and adjustable headgear (not shown). The function of the nasal pillow/mask 15 may be described by three distinct states: inhalation, exhalation, and apnea, depicted in FIGS. 5, 6, and 7, respectively (where only one inspiration one-way valve membrane and seat are shown) and again in FIGS. 8A-8C, 9A-9C, and 10A-10C respectively (where two inspiration one-way valve membranes and seats are shown).

In various example embodiments, the nasal pillow/mask 15 may begin to function as soon as the device is properly affixed and the blower box is set to the user's prescribed pressure, e.g., 0-20 cm $H_2O$. The device state of "inhalation" starts when the user inhales, as depicted in FIGS. 5 and 8A-8C. As the user inhales, inlet pressure one-way valve membrane 40 and inspiration one-way valve membranes 45A, 45B open and both ambient room air 80 and pressurized blower air 90 enter the cavity 65 at an inspiration cavity pressure 93, and that air flows through nasal interface 70A, 70B to the user as inspiration nasal air stream 85. Inhalation also causes the pressurized blower air 90 to create a net positive pressure 75 over the expiration valve membrane 35, causing it to sealably close against expiration valve seat 30. Since the expiration valve membrane 35 may be formed from a soft, flexible, compliant material, it advantageously makes little to no noise when it moves and engages and disengages the valve seat 30. This helps the user go to sleep and increases effectiveness by increasing user compliance with usage regimens.

Figure 5:
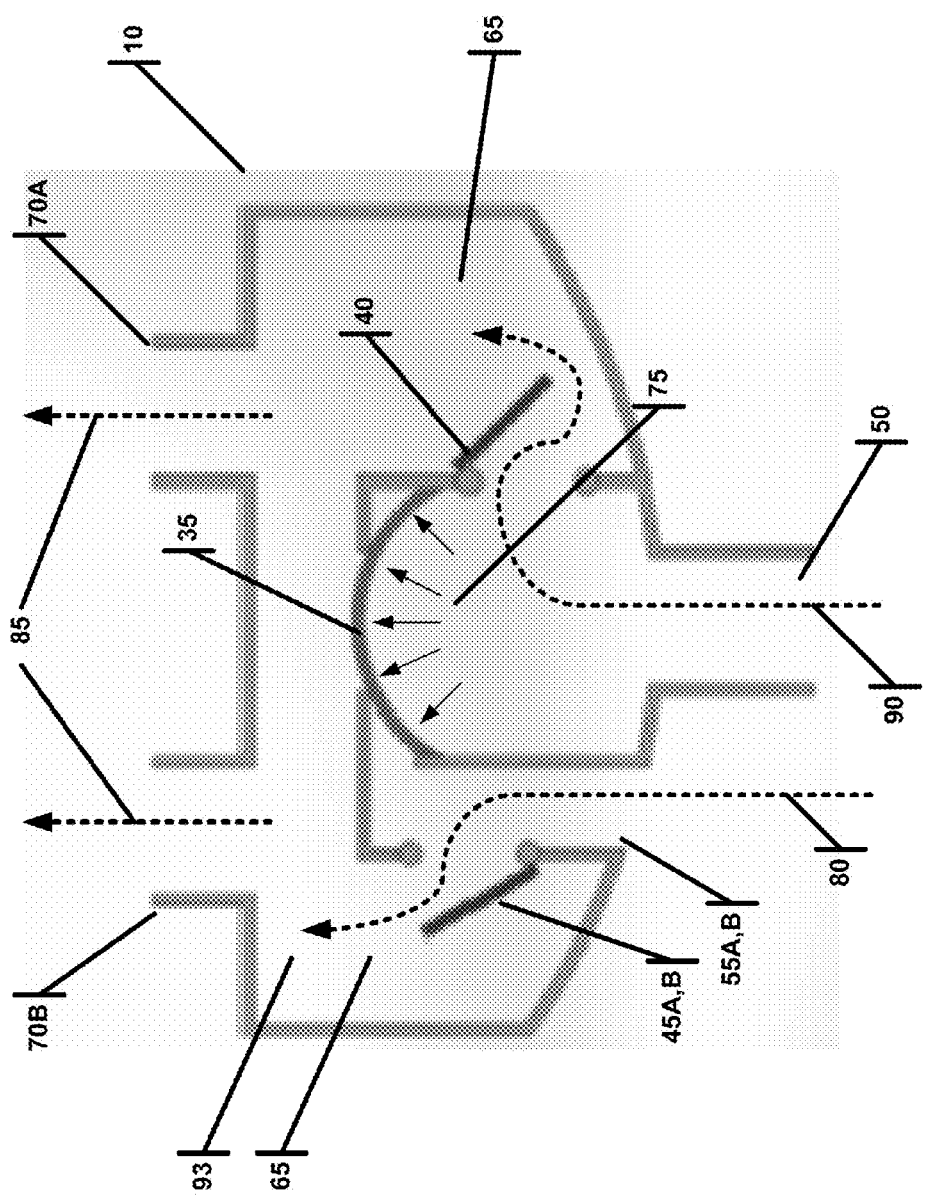
FIG. 5 is a schematic functionally depicting various aspects of an example CPAP apparatus operating during inhalation, according to various example embodiments.
Figure 6:
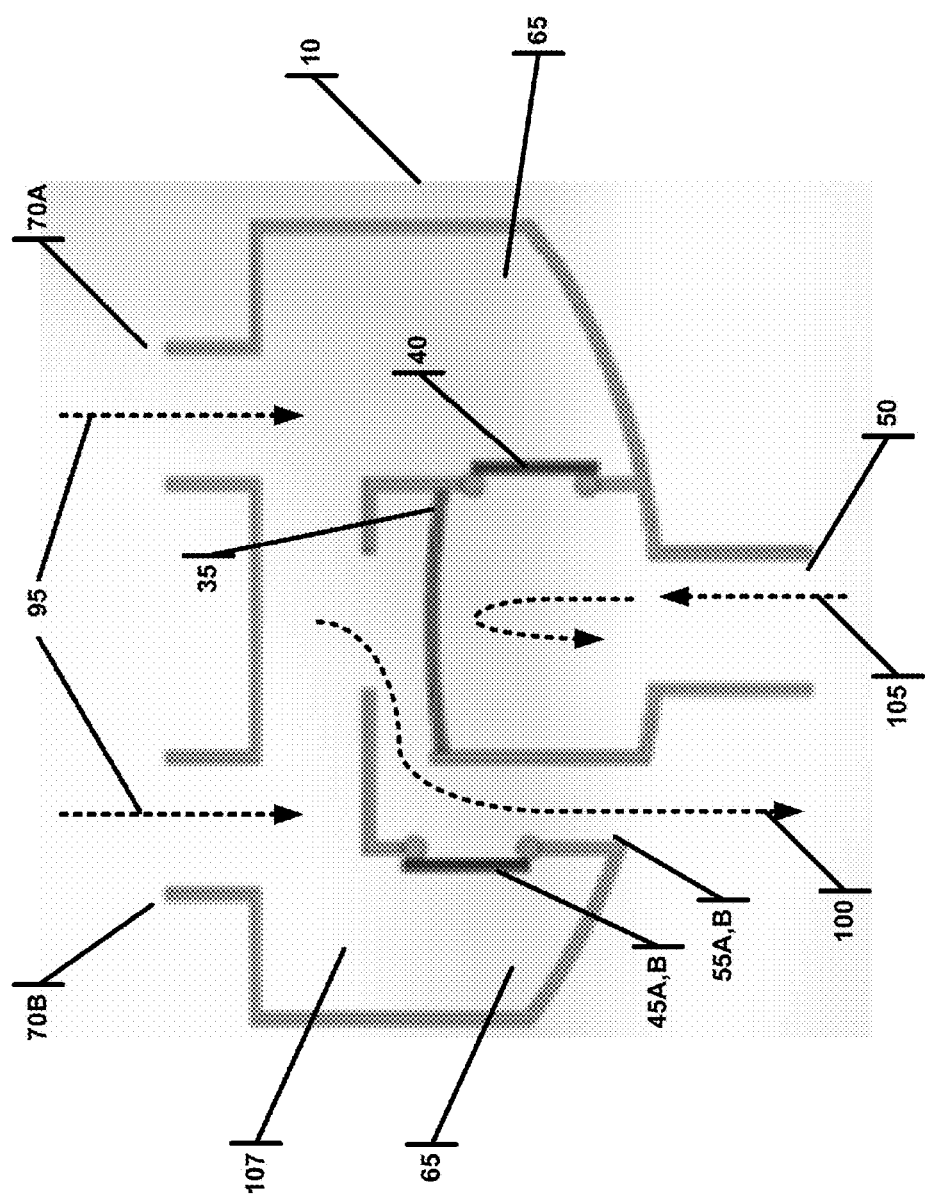
FIG. 6 is a schematic functionally depicting various aspects of an example CPAP apparatus operating during exhalation, according to various example embodiments.
Figure 7:
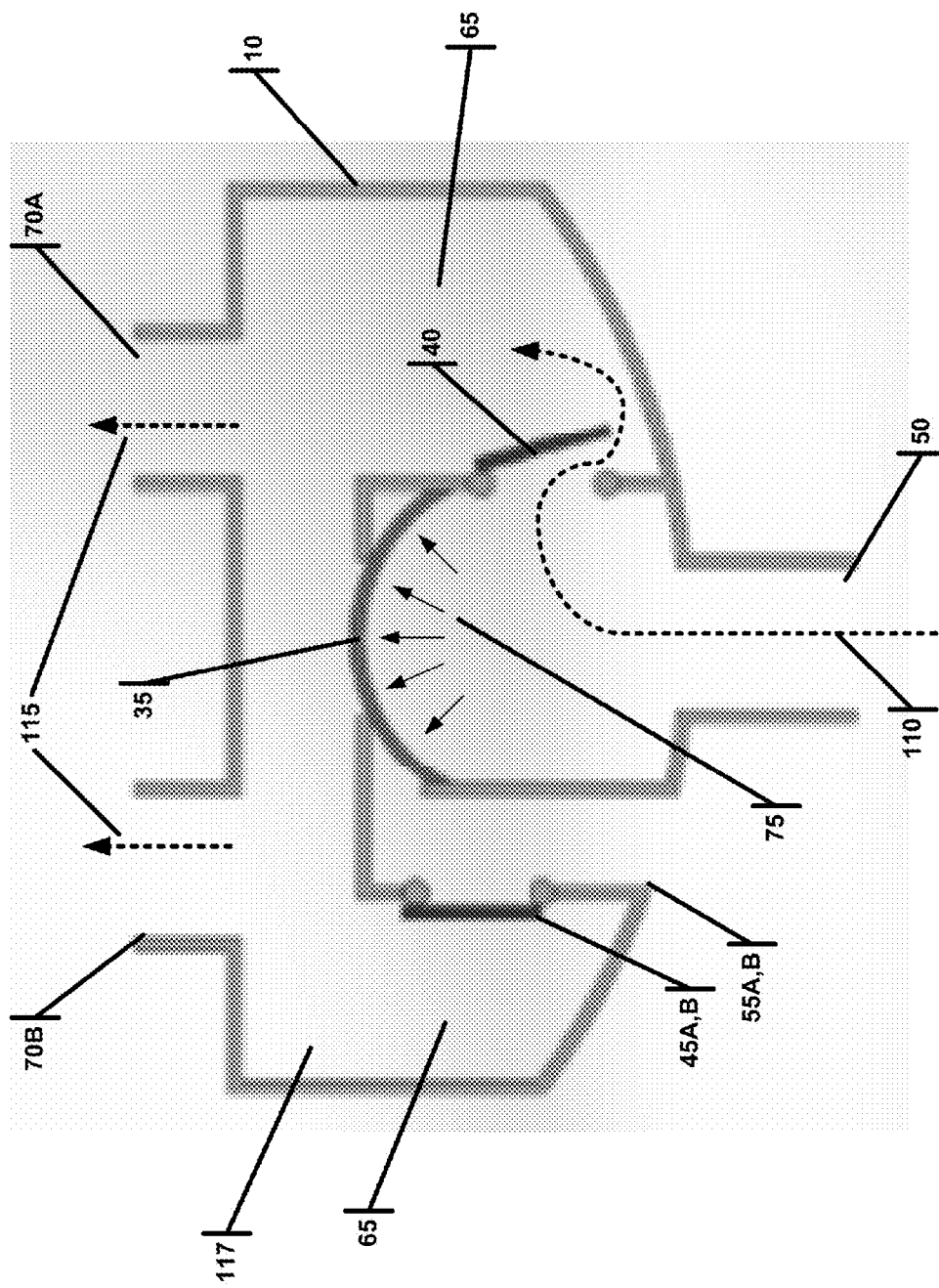
FIG. 7 is a schematic functionally depicting various aspects of an example CPAP apparatus operating during apnea, according to various example embodiments.
Figure 8:
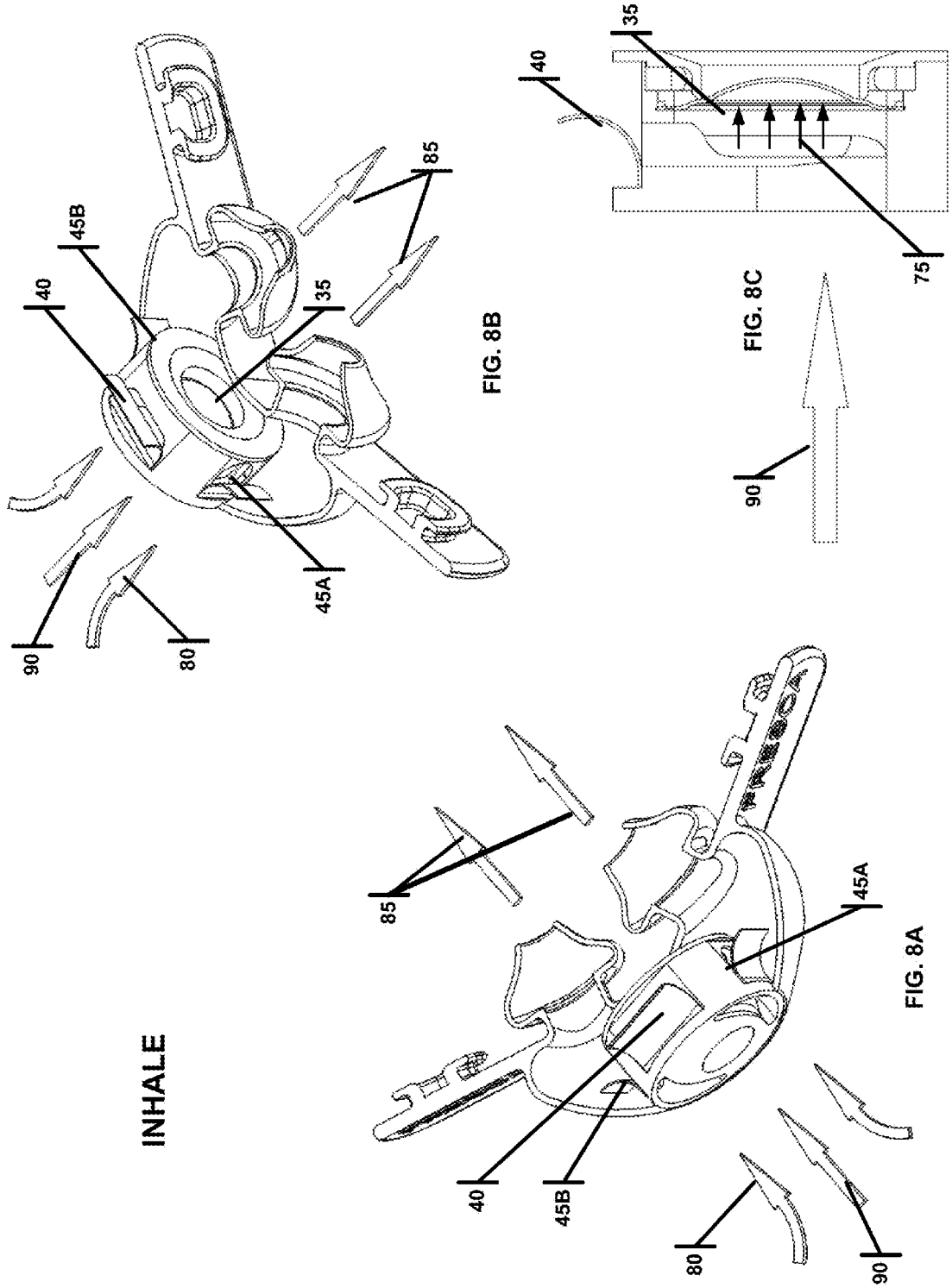
FIG. 8A is a front perspective section view of the example CPAP apparatus of FIG. 1, depicted operating during inhalation according to various example embodiments.
FIG. 8B is a rear perspective section view of the example CPAP apparatus of FIG. 1, depicted operating during inhalation according to various example embodiments.
FIG. 8C is a section side view taken through the middle of the example valve cartridge of FIG. 2A, depicted operating during inhalation according to various example embodiments.
Figure 9:
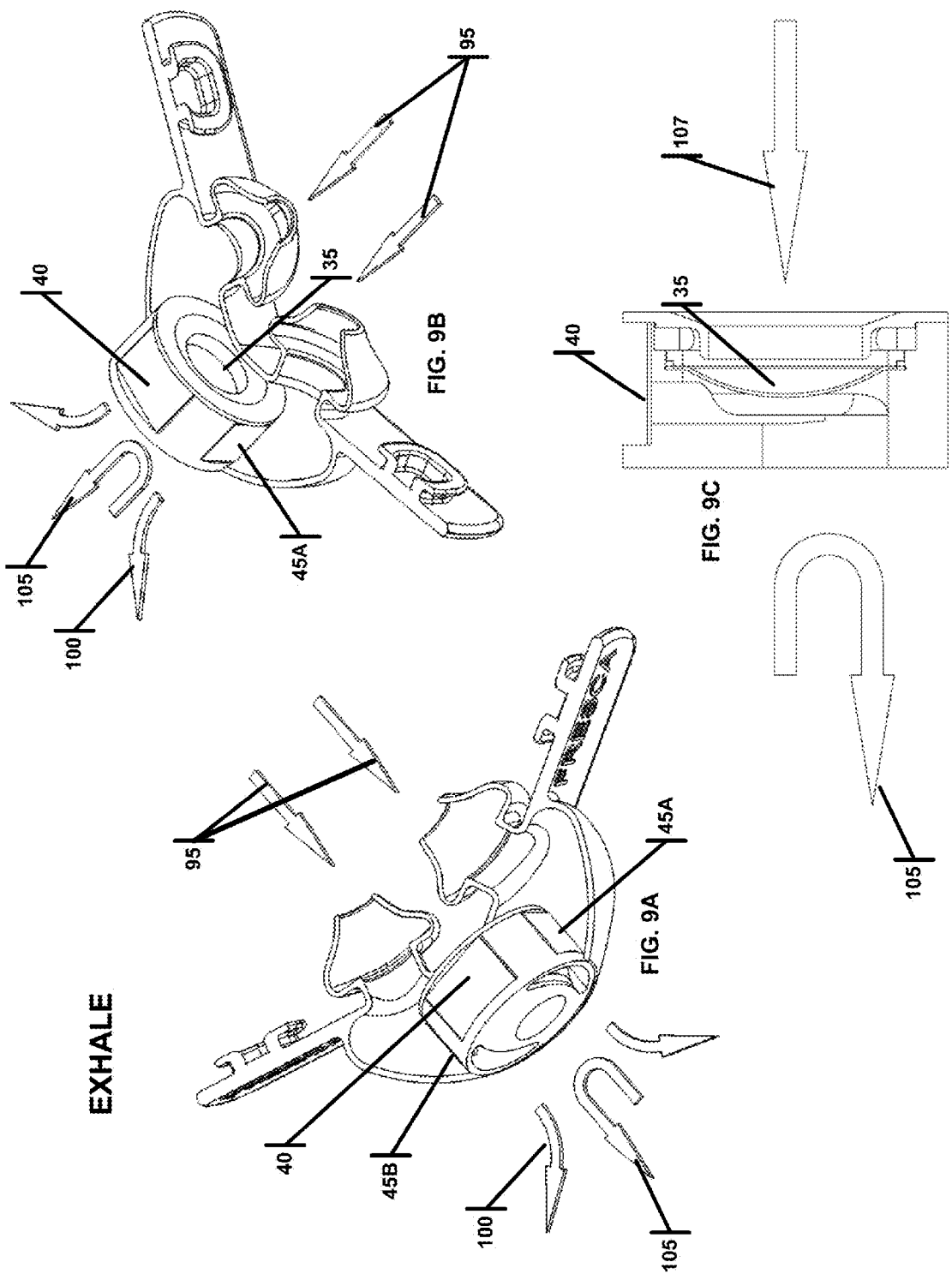
FIG. 9A is a front perspective section view of the example CPAP apparatus of FIG. 1, depicted operating during exhalation according to various example embodiments.
FIG. 9B is a rear perspective section view of the example CPAP apparatus of FIG. 1, depicted operating during exhalation according to various example embodiments.
FIG. 9C is a section side view taken through the middle of the example valve cartridge of FIG. 2A, depicted operating during exhalation according to various example embodiments.
Figure 10:
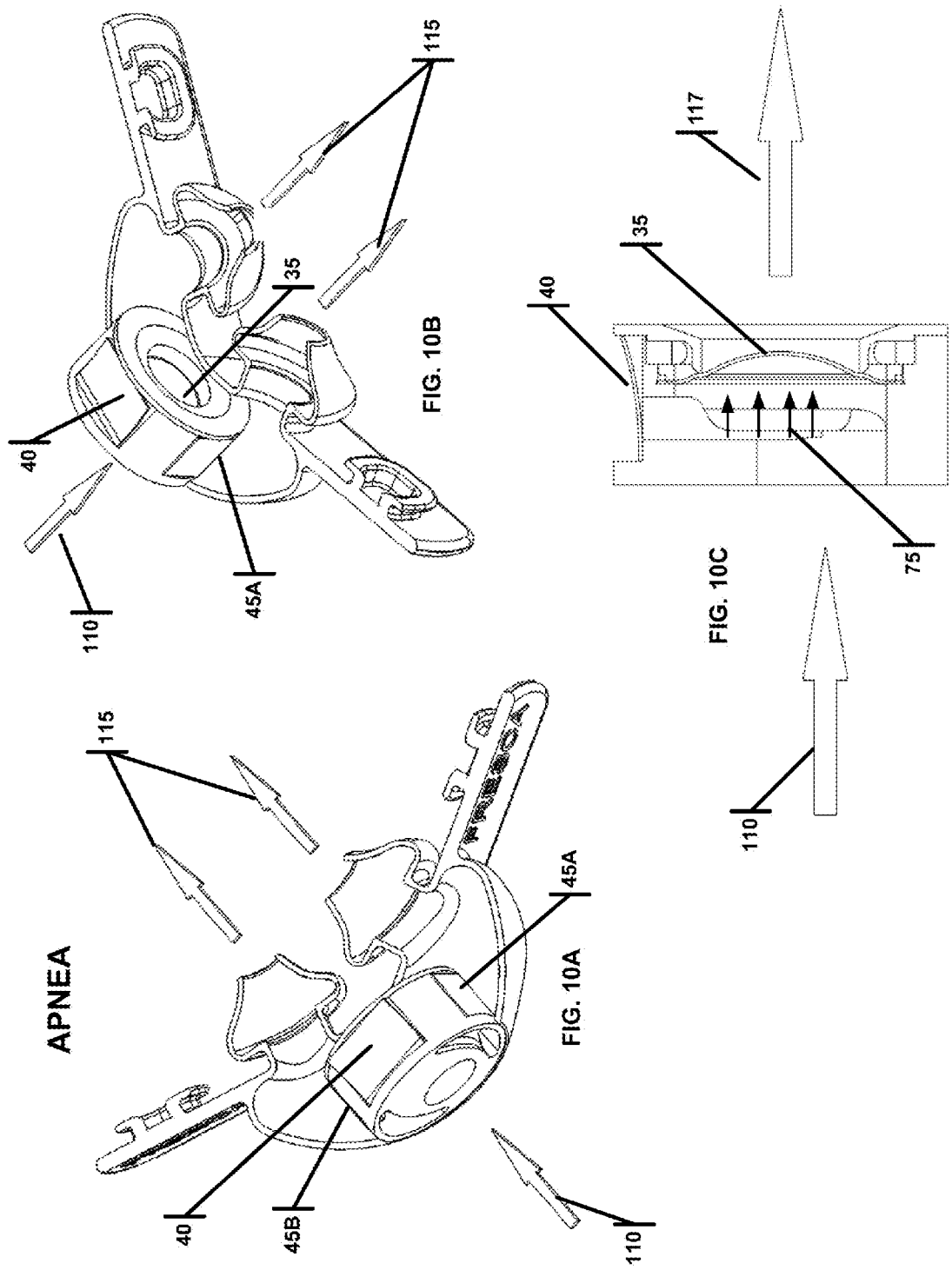
FIG. 10A is a front perspective section view of the example CPAP apparatus of FIG. 1, depicted operating during apnea according to various example embodiments.
FIG. 10B is a rear perspective section view of the example CPAP apparatus of FIG. 1, depicted during operating apnea according to various example embodiments.
FIG. 10C is a section side view taken through the middle of the example valve cartridge of FIG. 2A, depicted operating during apnea according to various example embodiments.

As depicted in FIG. 5, the expiration valve membrane 35 is sealably closed against expiration valve seat 30 because of a net force differential across the expiration valve membrane 35 in the direction of positive pressure 75, but only when the expiration valve membrane 35 is closed against seat 30, as shown in FIGS. 5 and 7. Once the expiration valve membrane 35 is closed against seat 30, this net force differential tends to bias expiration valve membrane 35 closed against seat 30 until the pressure in the cavity 65 increases above the pressure of blower air 90. At which time the expiration valve membrane 35 begins to open and unseat from seat 30, causing the expiration valve membrane 35 to open.

After inhalation, the user will begin to exhale. The state of exhalation starts when the user exhales, as depicted in FIGS. 6 and 9A-9C. Exhalation causes the pressure inside the pillow/mask 15 to rise up to and slightly higher than the blower box setting, thereby causing the inlet pressure one-way valve membrane 40 and inspiration one-way valve membranes 45A, 45B to close. With the inlet pressure one-way valve membrane 40 closed, an expiration positive pressure air stream 105 builds pressure in the inlet pressure port 50. This pressurized air 105 applies a force to the expiration valve membrane 35, urging it toward the expiration valve seat 30, and sealing it against the expiration valve seat 30 until the expiration nasal air stream 95 builds up enough pressure in the cavity 65 to overcome the force of pressurized air 105 and unseat expiration valve membrane 35 from expiration valve seat 30, thereby permitting the user to exhale, via open expiration ambient air stream 100 flowing out into the room through ambient pressure ports 55A, 55B. This is how the present system governs the exhalation or expiration cavity pressure 107; i.e., it is a direct and passive function of the amount of blower pressure 105. Accordingly, a blower set at different pressure settings will pressurize the expiration valve membrane 35 to different resistances. A lower blower box setting results in a lower resistance to unseating expiration valve membrane 35 from expiration valve seat 30, and thus causes a lower expiration cavity pressure 107. A higher blower box setting results in a higher resistance to unseating expiration valve membrane 35 from expiration valve seat 30, and thus causes a higher expiration cavity pressure 107. This unitary nasal pillow/mask 15 system can thus automatically and passively react to a multitude of blower box pressure settings. It also is contemplated that the nasal pillow/mask 15 can react to real-time changes in the blower box pressure setting. For example if the blower box has ramps, pressure relief, or dynamically titrates pressure, the nasal pillow/mask 15 should be able to instantly react appropriately.

If the user is sleeping normally, the user will finish exhalation and begin a new inhalation breath.

However, if either inhalation or exhalation is stopped, for instance by OSA, the nasal pillow/mask 15 will automatically enter into a state of "apnea treatment," as depicted in FIGS. 7 and 10A-10C. In this state the user is neither inhaling nor exhaling, so the expiration valve membrane 35 is sealably seated against expiration valve seat 30 by apnea positive pressure air stream 110 in the inlet pressure port 50. Apnea positive pressure air stream 110 quickly builds up in the inlet pressure port 50 to a higher pressure than the initial apnea cavity pressure 117 in the cavity 65, causing the inlet pressure one-way valve membrane 40 to open, thereby pressurizing the cavity 65 and causing inspiration one-way valve membranes 45A, 45B to close. Air from the blower 110 then builds up pressure 117 in the interior 65 of the nasal pillow/mask 15 to the pressure set at the blower box. The pressure 117 inside the mask 15 will then splint the user's airway, and the air from the blower box will flow through nasal interface 70A, 70B to the user as apnea nasal air stream 115, allowing the user to return back to breathing. Notably, only a minimal air flow is required from the hose, just enough to achieve a "dead-headed" pressure of the blower box or a minimal flow necessary to achieve pressure and make up for any small system leaks.

Figure 11:
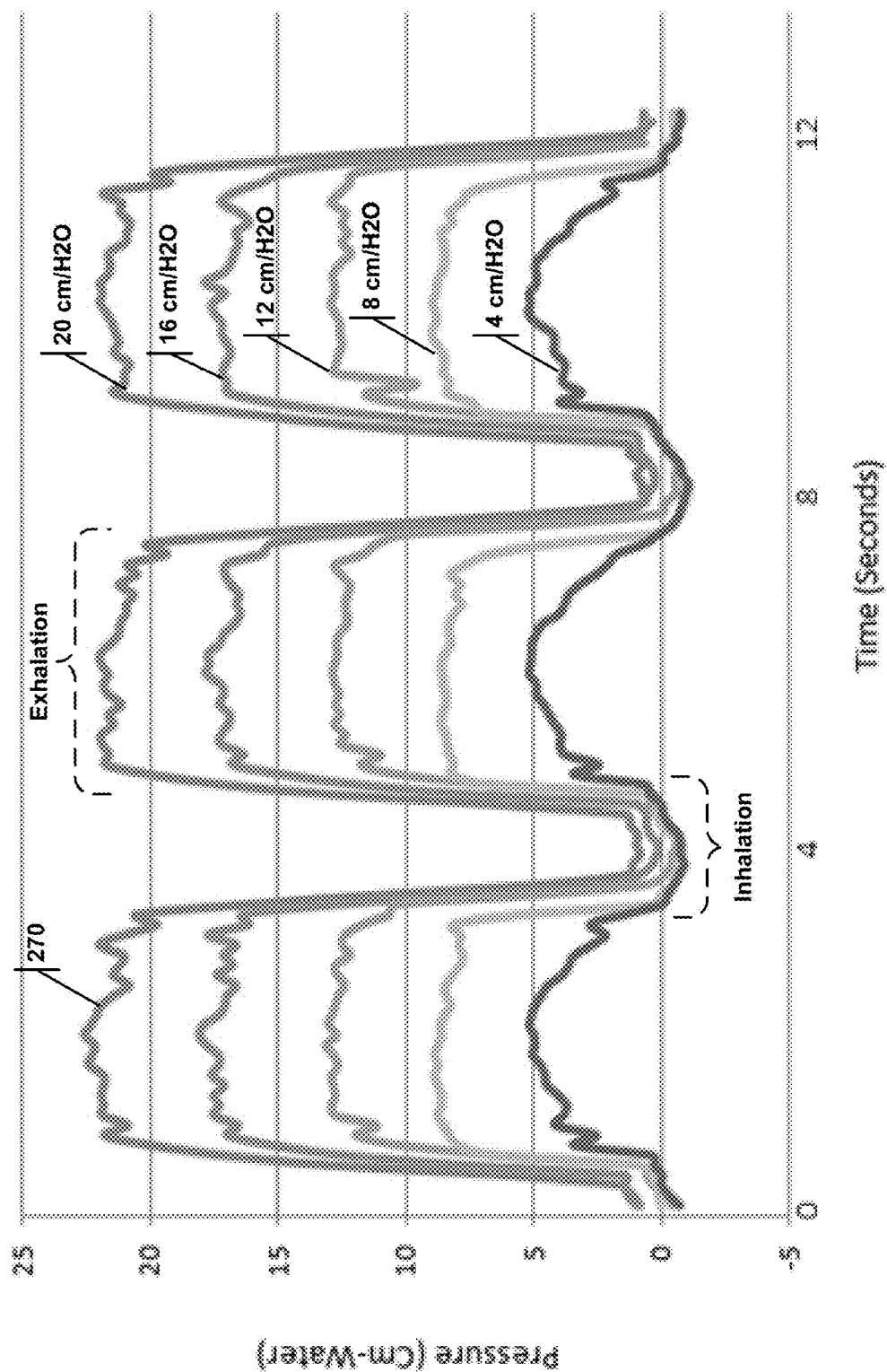
FIG. 11 is a graph of example breathing cycle pressures inside an example CPAP apparatus operating at different blower settings.
Figure 12:
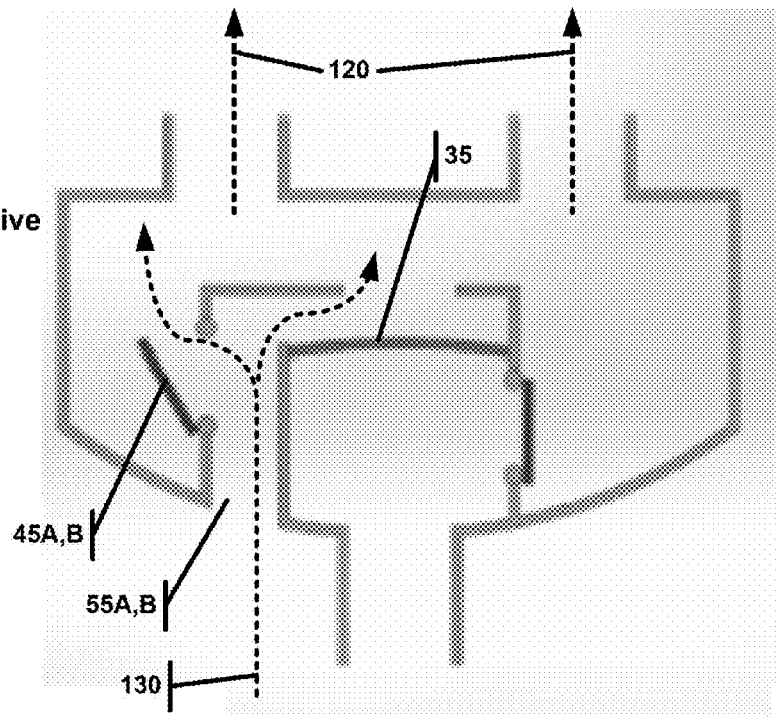
FIG. 12 is a schematic functionally depicting various aspects of an example CPAP apparatus during inhalation when the blower is off, according to various example embodiments.
Figure 13:
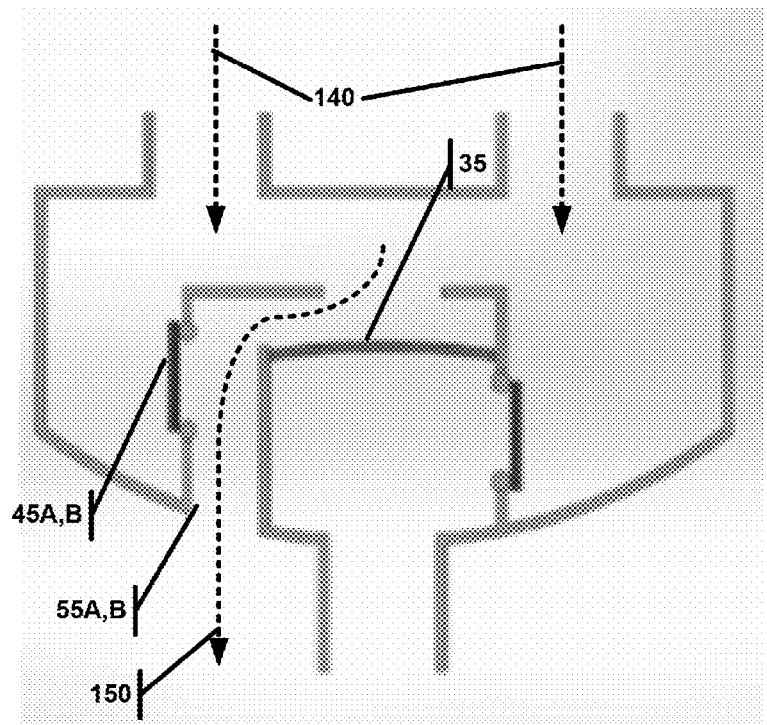
FIG. 13 is a schematic functionally depicting various aspects of an example CPAP apparatus during exhalation when the blower is off, according to various example embodiments.

Turning to FIG. 11, depicted are breathing curves obtained from using an example embodiment of a nasal pillow/mask 15 and system as disclosed herein, using a Harvard Breathing Apparatus at the following settings: Tidal Volume=500 ml Ventilation Frequency=20 breaths/min; Sample Time Constant 0.10 s; Ventilation Pressure 12.5 and 20.0 cm H2O; Inspiratory/Expiratory Phase Time Ratio 1:2.

Shown in FIG. 11 are five sets of pressures 270 measured in the cavity 65 of the nasal pillow/mask 15 for a series of three breaths. The five tracings of cavity pressures 270 are unique breath responses obtained from five corresponding settings on the CPAP blower box. Specifically, moving from the top of the page to the bottom in FIG. 11, the CPAP blower box settings were 20, 16, 12, 8, and 4 [cm $H_2O$]. This graph demonstrates an inhalation starting at barely below atmospheric pressure (using 0 cm $H_2O$ as atmospheric pressure), then rapidly reaching a therapeutic pressure as set by the blower box, maintaining that therapeutic pressure during exhalation, and rapidly returning to a sub low pressure on the next inhalation.

As depicted in FIGS. 17A-17D, when an apnea or OSA occurs (depicted by the dashed line), whether at the start of or during inspiration (FIGS. 17A and 17D) or expiration (FIGS. 17B and 17C), the pressure 270 measured in the cavity 65 of the nasal pillow/mask 15 will almost instantaneously reach and maintain the blower box pressure 280 (which is set at 10 cm/H2O). This constantly-pressurized state splints the airway and maintains this pressure 280 until the next inhalation occurs, as described herein. In contrast, a conventional CPAP system would trace a relatively constant pressure line 280 at the blower box pressure setting at all times, regardless of whether an apnea or OSA was occurring. Accordingly, conventional CPAP systems do not provide a significant sinusoidal tracing nor do they achieve a low pressure state during inhalation.

Since the present system is so sensitive and quick-reacting, in certain applications it may be appropriate to use it with a blower or airflow generator that need not run continuously, but rather is only activated as needed, for instance immediately upon detection of OSA. This option is possible with the present system in part because its unique valving system provides the additional feature of allowing a user to breathe normally while wearing it when there is no airflow or pressure being provided to the inlet port 50 by a blower. This is demonstrated in FIGS. 12 and 13, which show that when there is no airflow or pressure being provided to the inlet port 50 by a blower, the expiration valve membrane 35 will automatically move to its neutral position, which is unseated from the expiration valve seat 30, thereby opening a breathing path for the user. Specifically, upon inhalation, non-positive pressure inspiration ambient air flow 130 may travel through ambient pressure ports 55A, 55B, providing the user with non-positive pressure inspiration nasal air flow 120. Further facilitating inhalation, inspiration one-way valve membranes 45A, 45B will open upon inhalation, providing increased non-positive pressure inspiration ambient air flow 130 through ambient pressure ports 55A, 55B, thus providing the user with increased non-positive pressure inspiration nasal air flow 120. It is also possible that, depending on the pressure in the cavity and the construction of the expiration valve membrane 35, that the expiration valve member 35 may seat with the expiration valve seat 30 during inhalation, thus all airflow would travel through the ambient pressure ports 55A, 55B and through the inspiration one-way valves—i.e., the membranes 45A, 45B are opened. And upon exhalation, non-positive pressure expiration ambient air flow 150 may travel past the open expiration valve membrane 35 and through ambient pressure ports 55A, 55B, providing the user with non-positive pressure expiration nasal air flow 140.

Since the present the nasal pillow/mask 15 does not require the blower to run continuously, in various example embodiments a CPAP blower may be initiated in response to a preset delay, or in response to a detected onset of sleep or attainment of a preselected sleep stage, to enable a user to fall asleep while the blower is off. Accordingly, various example aspects of an airflow generator with delayed onset will now be described with reference to FIGS. 14-16.

Currently, human sleep stages are typically determined using a laboratory-based measurement called polysomnography. In polysomnography, it is typical for several electroencephalogram readings to be taken (EEGs are the microvolt potentials generated by brain activity that can be measured at the scalp using electrodes), in addition to other parameters such as respiration, electrocardiogram (ECG), leg movements, and electro-oculograms (EGG). Based on work originally pioneered by Rechtschaffen and Kales (R&K), it is now conventional to score human sleep in 30-second epochs, and to label these epochs using sleep stage labels.

At present, the American Academy of Sleep Medicine defines the stages of sleep as:

Wake—this is when a person is fully awake, and is characterized by a positive dominant rhythm in the occipital EEG channel (when eyes are closed), typically in the range 8-14 Hz (often referred to as alpha waves).

Stage N1—this is the lightest stage of sleep, and is characterized by the appearance of some low amplitude waves at multiple frequencies interspersed with the alpha waves for more than 50% of an epoch. There may also be sharp vertex waves, some slow eye movements on the EGG and/or an overall lowering of the frequency of EEG.

Stage N2—this is a slightly deeper stage of sleep, and is marked by the appearance of sleep spindles and K-complexes, on a background of mixed frequency signals. Sleep spindles are bursts of higher frequency activity (e.g., greater than 12 Hz). K-complexes are distinct isolated bipolar waves lasting about 1-2 seconds.

Stage N3 is the deepest stage of sleep (in the original R&K classification, there were two distinct stages called Stage 3 and Stage 4). This is characterized by the appearance of slow waves (e.g., 1-2 Hz frequency) for at least 20% of an epoch.

Stage R (REM)—this is rapid eye movement sleep, and is apparent through the presence of distinct activity in the EOG signal. The EEG signals recorded are typically quite similar to Stage N1 or even wake.

An automated system for scoring polysomnogram data is described in U.S. Pat. No. 5,732,696 to Rapoport et al., which is incorporated herein by reference. The system uses a computer to look for elemental patterns in the PSG data (such as the sleep spindles described above), and then uses a probabilistic weighting to score each epoch. However this approach to the problem of determining sleep stages is limited by the technical difficulty of measurement of a full set of polysomnogram signals, and hence is difficult and cumbersome to implement for more than a single night.

A number of systems have provided alternative techniques for determining sleep stage. One approach is to use actigraphy, in which small motion sensors (e.g., accelerometers) are worn by a user, typically in a wristwatch configuration in some cases referred to as activity trackers. Such systems may be able to effectively distinguish between sleep and wake, but may not effectively distinguish between different sleep states.

US2006/0184056 (Heneghan et al.), which is incorporated herein by reference, describes a sleep monitoring system which uses an ECG signal which is processed to determine a status for each epoch, either apneic or normal.

WO2007143535 (Heneghan et al.), which is incorporated herein by reference, describes a system for monitoring physiological signs such as sleep state by monitoring motion, breathing, and heart rate signals obtained in a non-contact fashion. A classifier model is applied to the streams of data.

A system which combines ECG and respiration methods to determine simplified sleep stage is described in US20090131803 (Heneghan et al.), which is incorporated herein by reference. This combines signal characteristics derived from cardiogram and respiration signals, such as the amplitude modulation of the ECG signal and the dominant respiratory frequency in order to distinguish sleep from wakefulness.

WO2004112606 (Heneghan et al.), which is incorporated herein by reference, describes a method of detecting sleep apnea using trans-cervical bioimpedance measurements.

US2011/0124979 (Heneghan et al.), which is incorporated herein by reference, describes an approach to sleep monitoring using ECG and photoplethysmogram (PPG) data. These may be sensed using a Holter monitor and a pulse oximeter which are wearable in an ambulatory manner.

An approach in which cardiac R-R wave intervals are used to designate sleep as REM or non-REM is described in U.S. Pat. No. 5,280,791 to Lavie, which is incorporated herein by reference. A power spectrum of the cardiac R-R interval is calculated in order to determine the stages of sleep.

US2014/0088373 (Phillips et al.), which is incorporated herein by reference, discloses a system that is said to be able to differentiate between sleep states. A processor determines a sleep stage based on a combination of bodily movement and respiration variability. The determination of sleep stages may distinguish between deep sleep and other stages of sleep, or may differentiate between deep sleep, light sleep and REM sleep. The bodily movement and respiration movement signals may be derived from one or more sensors, such as a non-invasive sensor (e.g., a non-contact radio-frequency motion sensor or a pressure sensitive mattress).

Any of a variety of commercially available wearable or portable activity trackers are also equipped with sleep detection capabilities, such as: FIT BIT (Fitbit Inc. 405 Howard Street, San Francisco, Calif. 94105); SENSE and SLEEP PILL (Hello Inc, 1660 17th Street, San Francisco, Calif. 94107); Beddit (Misfit); MisfitShine (Misfit); and Withings Aura™, for example.

Conventional breathing devices such as CPAP systems must have the blower operating while the user is wearing the mask. The blower is typically set to a minimum of 4 cm $H_2O$. This is necessary because without the blower delivering fresh air, the user re-breaths residual exhalations that migrate into and out of the hose. The blower is not continuously flushing out the stale air from the hose when turned off in conventional CPAP. The blower creates noise and perceptible air flow, interfering with the wearer's ability to go to sleep.

The system of the present invention eliminates the need for the blower to operate while the user is attempting to go to sleep. It may also have a much smaller caliber hose, such as 50% smaller in diameter. This has a significant volume reduction, hence significantly less potential for "re-breath air" to reside. Also a preferred embodiment has a one-way flapper valve on the air supply path which prevents exhaled breath from migrating into the hose. While prior art systems need to maintain around a minimum flow rate corresponding to 4 cm $H_2O$ of pressure while the user tries to go to sleep over the noise, the blower in the system of the present invention can be shut off while the user is trying to go to sleep. The blower is instead not turned on until a delayed start time T. Time T can be preselected as a delay from initiation of the clock and measured in time such as in minutes or hours. Alternatively T can be a set time of day programmed in by the user or care giver, based upon their experience how long it takes that user to go to sleep, or a time at which the onset of sleep is detected using any of a variety of sleep detectors.

Figure 14:
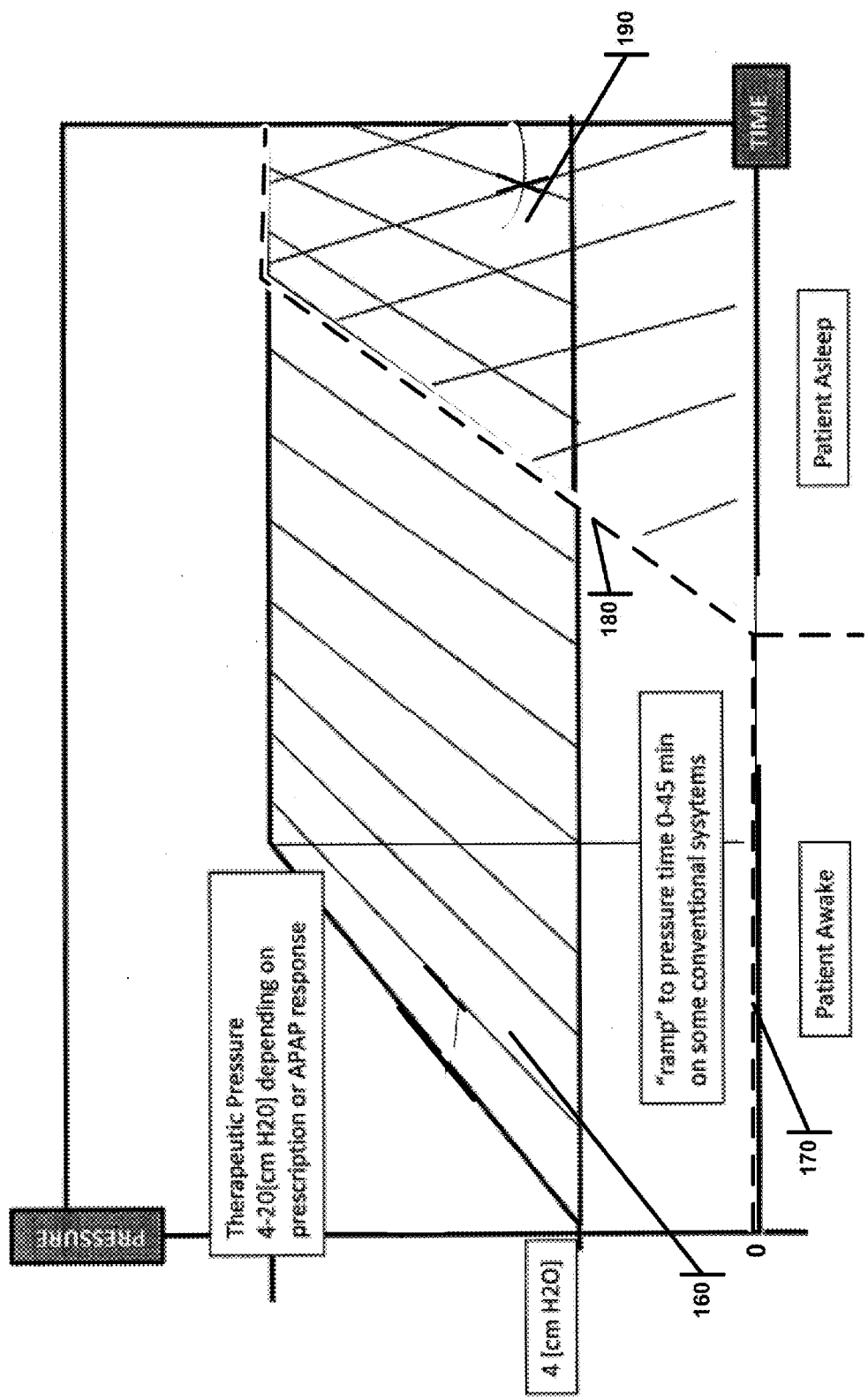
FIG. 14 is a chart showing example pressures applied by an example CPAP system at various times, according to various example embodiments.

Graphically, conventional systems must operate in the hashed area 160 shown in FIG. 14, with an air flow of at least about 4 cm H20 at all times that the mask is worn by the user, and ramping to higher flow rates.

The present system operates on the datum line 170 and in the hashed area 190 shown above the datum line 170. The air flow rate from the blower can be zero while the user is awake, and the blower can remain off until after the user has fallen asleep. After the onset of a sleep state, the blower can turn on and subsequently ramp up 180 to the desired therapeutic flow rate. This is advantageous because it eliminates the sensation of forced airflow, and eliminates noise from the blower box, while the user is trying to go to sleep. Also, this preserves the ability to speak naturally prior to sleep.

The present system can work with the blower off indefinitely. In one embodiment the blower is off at the start of use and turns on at a preset time delay following activation of the timing cycle. The time delay can either be programmed into the machine or selectable by the physician or user (an off time could also be set for an anticipated wake-up). The user may select or input a delay such as at least about 5 minutes, or at least about 10, 15, or 30 minutes, or up to an hour or more, for example. The blower will automatically turn on at delayed start time T and begin to ramp up in air flow when the preset delay period has expired. Alternatively, the user can select a start time of day such as 10:00 PM or 11:00 PM by which time the user expects to be asleep.

Alternatively, the blower can turn on in response to a determination that the user has fallen asleep or reached a particular sleep stage. Sleep sensors may be employed to determine when the user achieves a sleep state. In response to the detection of the onset of sleep, the blower is turned on and ramps to the desired therapeutic flow rate. The sleep sensors may be carried by the system, or may be a remote device that is in wireless or wired communication with the system. Any of the sleep detection devices discussed elsewhere herein can be utilized to determine the onset of sleep.

Thus, one or more biometric monitoring devices may automatically detect or determine when the user is attempting to go to sleep, is entering sleep, is asleep, and/or is awoken from a period of sleep. In such embodiments, the biometric monitoring device may employ physiological sensors to acquire data and the data processing circuitry of the biometric monitoring device may correlate a combination of heart rate, heart rate variability, respiration rate, galvanic skin response, motion, skin temperature, and/or body temperature data collected from sensors of the biometric monitoring device to detect or determine if the user is attempting to go to sleep, is entering sleep, is asleep, and/or is awoken from a period of sleep. For example, a decrease or cessation of user motion combined with a reduction in user heart rate and/or a change in heart rate variability may indicate that the user has fallen asleep. Subsequent changes in heart rate variability and galvanic skin response may then be used by the biometric monitoring device to determine transitions of the user's sleep state between two or more stages of sleep (for example, into lighter and/or deeper stages of sleep). Motion by the user and/or an elevated heart rate and/or a change in heart rate variability may be used by the biometric monitoring device to determine that the user has awoken. Additional details can be found in US patent publication 20140278229 to Hong, et al., assigned to Fitbit, Inc., the disclosure of which is hereby incorporated in its entirety herein by reference.

The CPAP system of the present invention thus includes an input for receiving a signal indicative of the onset of sleep or a change in a stage of sleep. The input may be a wired port or a wireless port. Preferably but not necessarily, a wireless port is provided in the form of a transceiver for wireless pairing with any of a variety of commercial devices capable of determining sleep state.

These devices include any of a variety of commercial activity trackers (e.g., Fitbit, Jawbone, Under Armour, UP, Resmed S+) a sleep detection bed (e.g., Sleep Number), or any of a variety of dedicated sleep detection systems that can either be integrated into the device or separate but connectable via wireless or hard wired connection.

In another embodiment, sleep/apnea sensors are employed to turn the machine on only when both sleep and apnea are occurring. In either case, the sleep sensors could also do the opposite function and turn the blower off when waking is sensed. Suitable sleep apnea detection systems are disclosed in U.S. Patent Publication No. 2014/0200474, the disclosure of which is incorporated by reference in its entirety herein.

The advantages of being able to wear a CPAP mask with no blower operating include: comfort from no forced airflow while awake; talking without the difficulty of forced air; less noise while attempting to sleep; and reduction of wasted power, in particular battery power.

Figure 15:
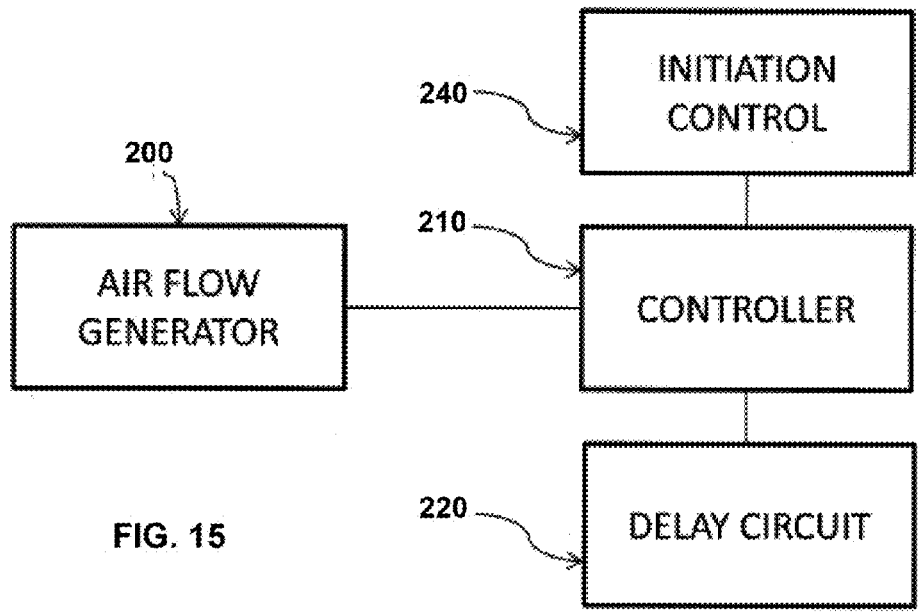
FIG. 15 is a diagram depicting example relationships among example components of an example CPAP system operated in part by a delay circuit, according to various example embodiments.

Referring to FIG. 15, the present system may comprise a mask/hose and a blower box with an air flow generator 200, a controller 210 and a delay circuit 220. An initiation control 240 is provided for the user to initiate a delay cycle. The initiation control can be a button, switch, touch screen or other control.

Figure 16:
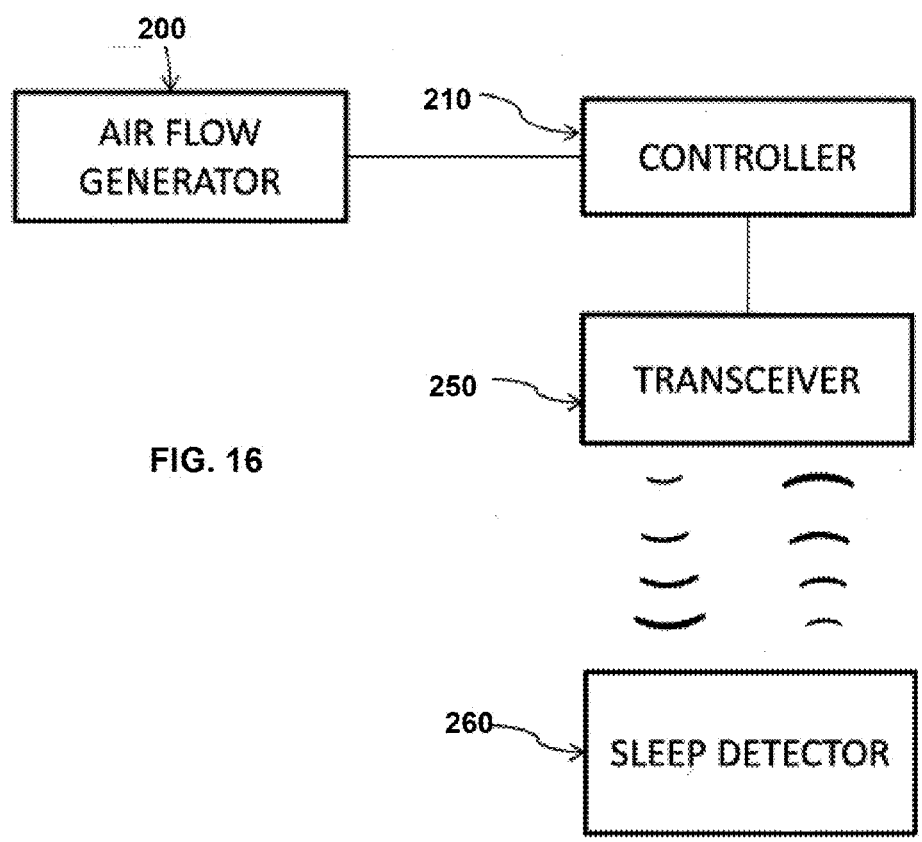
FIG. 16 is a diagram depicting example relationships among example components of an example CPAP system operated in part by a sleep detector, according to various example embodiments.
Figures 17A, 17B:
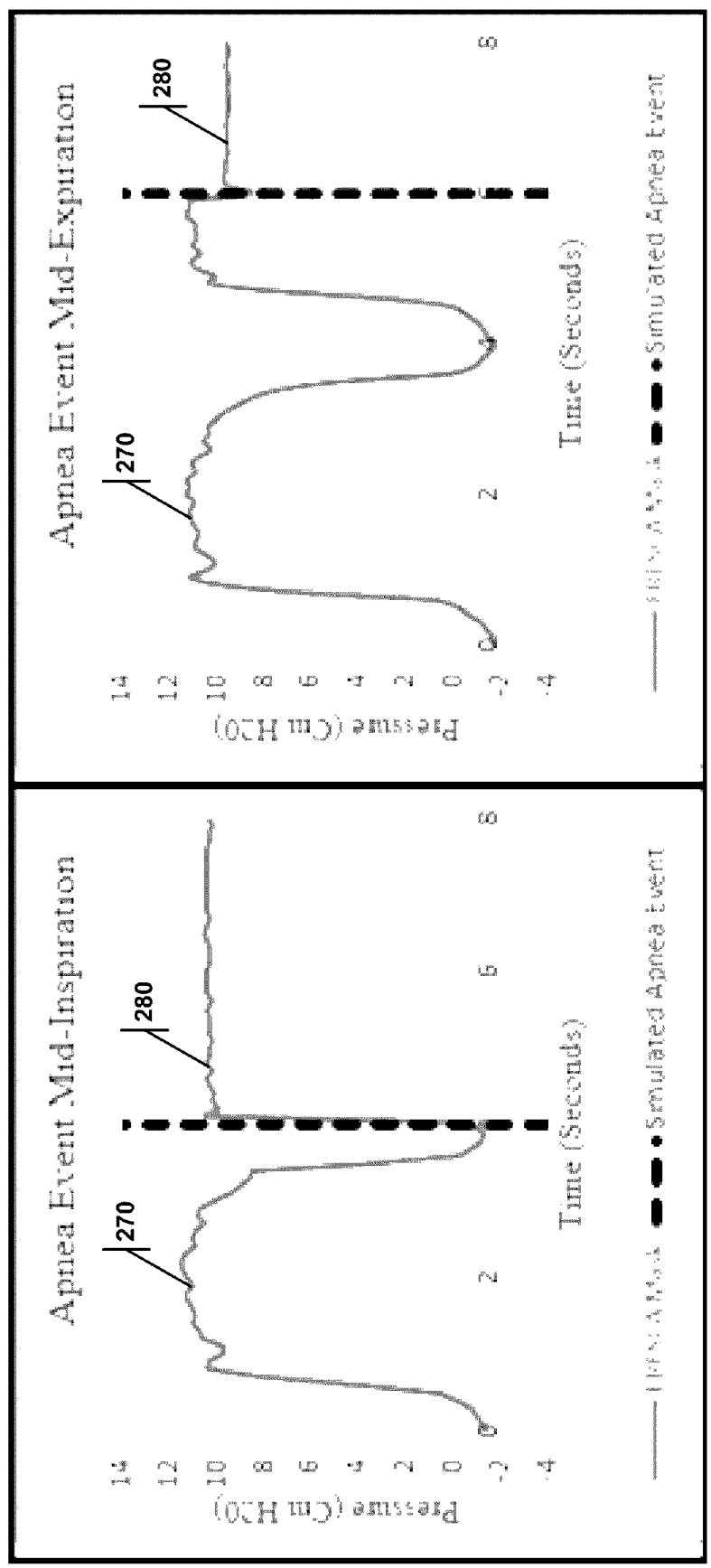
FIG. 17A is a chart showing example pressures applied by an example CPAP system during an apnea event occurring during mid-inspiration, according to various example embodiments.
FIG. 17B is a chart showing example pressures applied by an example CPAP system during an apnea event occurring during mid-expiration, according to various example embodiments.
Figures 17C, 17D:
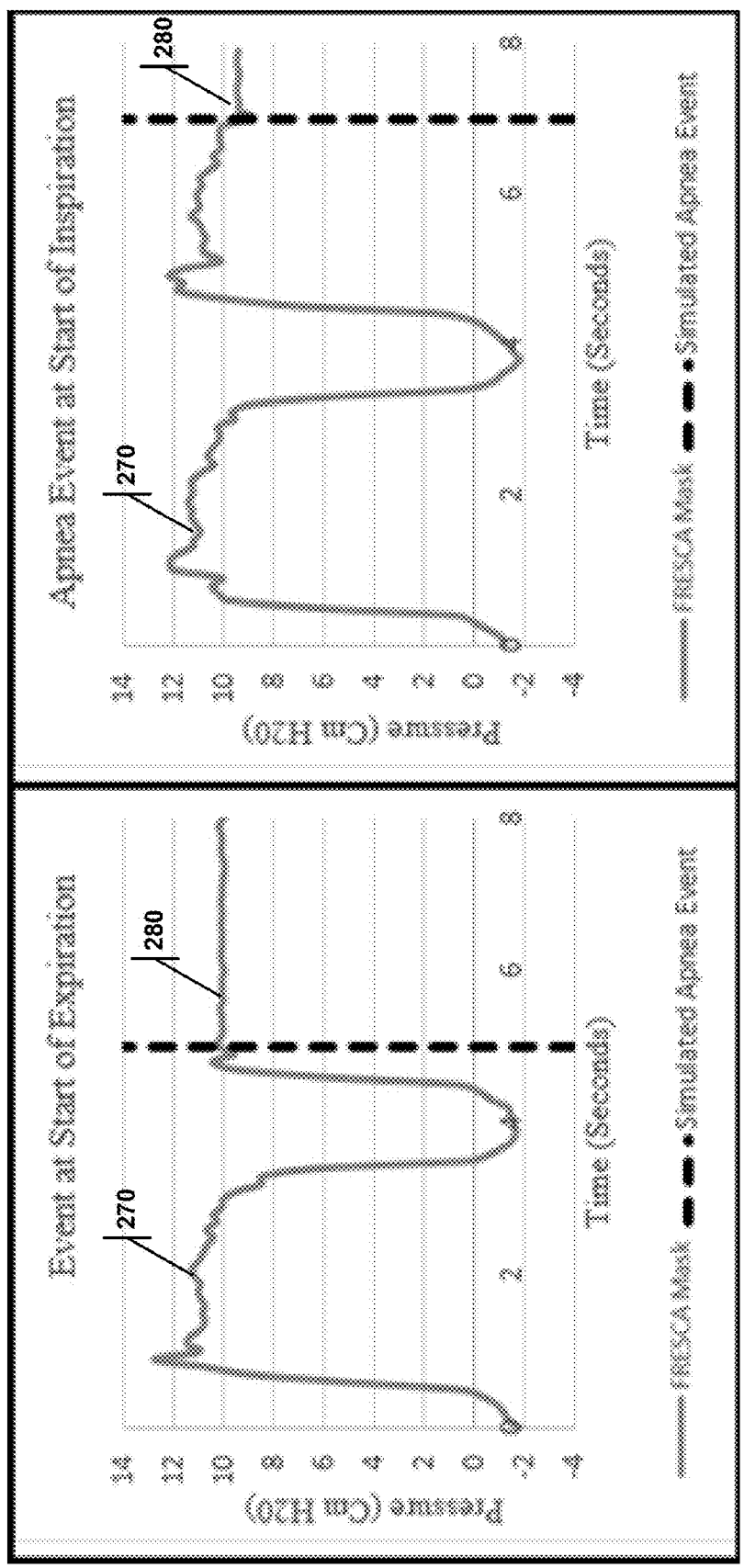
FIG. 17C is a chart showing example pressures applied by an example CPAP system during an apnea event occurring during start of expiration, according to various example embodiments.
FIG. 17D is a chart showing example pressures applied by an example CPAP system during an apnea event occurring during start of inspiration, according to various example embodiments.

The present system has the ability to communicate with accessory devices. This communication can come from mechanical or pneumatic feedback, preferably but not necessarily electronic communication transmitted over a wire or wireless. Most preferably but not necessarily the present system has "Bluetooth" or other wireless communication with accessory sleep-detection devices. The communication features could be in any component, most preferably but not necessarily in the blower box. Referring to FIG. 16, the controller 210 is in electrical communication with a transceiver 250 which may be permanently or removably carried by the housing as discussed herein. The transceiver 250 can be paired into wireless communication with a sleep detector 260.

The wireless communication module 250 and associated antenna carried by the CPAP device thus provide a wireless connection between the CPAP device and a paired sleep detection device 260 such as any of those discussed herein. Preferably but not necessarily the sleep detector is a wearable device such as an activity tracker. Pairing may be accomplished utilizing any of a variety of short-range wireless protocols appropriate for the particular sleep detection device, such as Wi-Fi, Zigbee, Bluetooth, wireless HDMI and/or IEEE 802.11 protocols (e.g., 802.11G, 802.11N, 802.11AC, or the like). Other examples of potential communication protocols include iBeacon, Z-Wave, WirelessHART/Dust Networks, ISA 100a, ISM-band-based channels, IMBI, ANT or ANT+, or other methods of communication.

For the purposes of the present disclosure, the term "ANT" is intended to include "ANT+ and refers to a proprietary wireless sensor network technology featuring a wireless communications protocol stack that enables semiconductor radios operating in the 2.4 GHz industrial, scientific, and medical allocation of the RF spectrum ("ISM band") to communicate by establishing standard rules for co-existence, data representation, signaling, authentication, and error detection. ANT is characterized by a low computational overhead and low to medium efficiency, resulting in low power consumption by the radios supporting the protocol.

For the purposes of the present disclosure, the term "Bluetooth®" refers to a wireless technology standard for exchanging data over short distances (using short-wavelength radio transmissions in the ISM band from 24000-2480 MHz) from fixed and mobile devices, creating personal area networks (PANs) with high levels of security. Created by telecom vendor Ericsson in 1994, it was originally conceived as a wireless alternative to RS-232 data cables. It can connect several devices, overcoming problems of synchronization. Bluetooth® is managed by the Bluetooth® Special Interest Group, which has more than 18,000 member companies in the areas of telecommunication, computing, networking, and consumer electronics. Bluetooth® was standardized as IEEE 802.15.1, but the standard is no longer maintained.

A wireless LAN may exist using a different IEEE protocol, 802.11b, 802.11g or possibly 802.11n. The defining characteristics of LANs, in contrast to WANs (wide area networks), include their higher data transfer rates, smaller geographic range, and lack of a need for leased telecommunication lines. Current Ethernet or other IEEE 802.3 LAN technologies operate at speeds up to 10 Gbit/s.

For the purposes of the present disclosure, the term "low powered wireless network" refers to an ultra-low powered wireless network between sensor nodes and a centralized device. The ultra-low power is needed by devices that need to operate for extended periods of time from small batteries with energy scavenging technology. Examples of low powered wireless networks are ANT, ANT+, Bluetooth Low Energy (BLE), ZigBee and WiFi.

For the purposes of the present disclosure, the term "ZigBee" refers to a specification for a suite of high level communication protocols used to create personal area networks built from small, low-power digital radios. ZigBee is based on an IEEE 802 standard. Though low-powered, ZigBee devices often transmit data over longer distances by passing data through intermediate devices to reach more distant ones, creating a mesh network; i.e., a network with no centralized control or high-power transmitter/receiver able to reach all of the networked devices. The decentralized nature of such wireless ad-hoc networks make them suitable for applications where a central node can't be relied upon. ZigBee may be used in applications that require a low data rate, long battery life, and secure networking ZigBee has a defined rate of 250 Kbit/s, best suited for periodic or intermittent data or a single signal transmission from a sensor or input device. The technology defined by the ZigBee specification is intended to be simpler and less expensive than other WPANs, such as Bluetooth® or Wi-Fi. Zigbee networks are secured by 128 bit encryption keys.

Suitable wireless pairing protocols between the CPAP device and remote activity tracker or other sleep detection device are disclosed in US patent publication 2014/0281547, entitled "Wireless Pairing of Personal Health Device with a Computing Device", the disclosure of which is hereby incorporated by reference in its entirety herein.

Since different currently available activity trackers may utilize different protocols (e.g., some may utilize Bluetooth, others may utilize ANT or ANT+), the communication module 250 carried by the CPAP device of the present invention is preferably but not necessarily able to pair utilizing any of a variety of protocols so that it can universally obtain sleep onset data from whatever device the user may choose to utilize. Thus, the communication module may be provided with a capability to communicate utilizing at least two and preferably but not necessarily at least three or four or more different protocols. It can be programmed to detect the appropriate protocol from a sleep detector in range and select that protocol automatically for a given activity tracker or other source device. Alternatively, a user may be provided with a choice from an array of different communication modules from which they can select the module capable of communication with their sleep onset detector. The selected module can then be plugged into a transceiver docking port on the CPAP device followed by pairing as is understood in the art. The CPAP device may thus be provided with a port for removably receiving the selected communication module.

The accessory devices that the present system communicates with can be various items that have the ability to sense sleep onset and or sleep stage. Exemplary accessory devices can sense sleep state in a variety of ways: movement, breath rate, blood pressure, heart rate, eye motion, temperature, sound, brain activity, physiological activity such as kidney function, GI function, hormone production and delivery. Such accessory devices may comprise a Fit Bit or other accessory device that already has sleep sensing capabilities, and may communicate, for instance wirelessly, with the blower box and tell it whether the person is asleep or awake, so that the blower box can respond by turning on or off based on the sleep state that is reported to it.

From observing changes in behavior and responsiveness, scientists have noted the following characteristics that accompany and in many ways define sleep: sleep is a period of reduced activity; sleep is associated with a typical posture, such as lying down with eyes closed in humans; sleep results in a decreased responsiveness to external stimuli; sleep is a state that is relatively easy to reverse (this distinguishes sleep from other states of reduced consciousness, such as hibernation and coma).

From observations of behavioral changes that accompany sleep and simultaneous physiological changes, scientists now define sleep in humans based on brain wave activity patterns and other physiological changes as described below.

Many physiological variables are controlled during wakefulness at levels that are optimal for the body's functioning. A person's temperature, blood pressure, and levels of oxygen, carbon dioxide, and glucose in the blood remain quite constant during wakefulness. During sleep, however, physiological demands are reduced and temperature and blood pressure drop. In general, many physiological functions such as brain wave activity, breathing, and heart rate are quite variable when a person is awake or during REM sleep, but are extremely regular when a person is in non-REM sleep.

For centuries, physicians believed that sleep was a period of brain inactivity, yet research over the last 60 years has shown us that the brain remains active during sleep. There is a progressive decrease in the activation or "firing" rate of most neurons throughout the brain as sleep progresses from wakefulness to non-REM sleep. Also, the patterns of neuron firing change from a seemingly random and variable activity pattern during wakefulness, to a much more coordinated and synchronous pattern during non-REM sleep.

During REM sleep (the stage of sleep most associated with dreaming) there is an increase in the firing rate of most neurons throughout the brain, as compared to non-REM sleep. In fact, the brain in REM sleep can even be more active than when awake. Patterns of brain activity during REM sleep are more random and variable, similar to during wakefulness. This pattern of brain activity during REM sleep probably underlies the intense dreaming that occurs during this state.

Through a process known as thermoregulation, the temperature of our body is controlled by mechanisms such as shivering, sweating, and changing blood flow to the skin, so that body temperature fluctuates minimally around a set level during wakefulness. Just before a person falls asleep, their body begins to lose some heat to the environment, which some researchers believe actually helps to induce sleep. During sleep, the body's central set temperature is reduced by 1 to 2° F. As a result, people use less energy maintaining their body temperature. It has been hypothesized that one of the primary functions of sleep is to conserve energy in this way.

Body temperature is still maintained, although at a slightly reduced level during non-REM sleep, but during REM sleep body temperature falls to its lowest point. Sleeping under a blanket during the usual 10-to 30-minute periods of REM sleep ensures that people do not lose too much heat to the environment during this potentially dangerous time without thermoregulation.

Breathing patterns also change during sleep. When a person is awake, breathing is usually quite irregular, since it is affected by speech, emotions, exercise, posture, and other factors. As a person progresses from wakefulness through the stages of non-REM sleep, their breathing rate slightly decreases and becomes very regular. During REM sleep, the pattern becomes much more variable again, with an overall increase in breathing rate.

One of the possible functions of sleep is to give the heart a chance to rest from the constant demands of waking life. As compared to wakefulness, during non-REM sleep there is an overall reduction in heart rate and blood pressure. During REM sleep, however, there is a more pronounced variation in cardiovascular activity, with overall increases in blood pressure, heart rate, and blood flow.

For the most part, many physiological activities are reduced during sleep. For example, kidney function slows and the production of urine is decreased. However, some physiological processes may be maintained or even increased during sleep. For example, one of the greatest changes induced by sleep is an increase in the release of growth hormone. Certain physiological activities associated with digestion, cell repair, and growth are often greatest during sleep, suggesting that cell repair and growth may be an important function of sleep.

One of the most notable but least understood characteristics of sleep is dreaming, during which a person's thoughts may follow bizarre and seemingly illogical sequences, sometimes random and sometimes related to experiences gathered during wakefulness. Visually intense dreaming occurs primarily during REM sleep. However, not all dreams occur during REM sleep. For example, night terrors actually occur during non-REM sleep.

Varying explanations for dreaming, as well as the meanings of dreams, have been offered by philosophers and psychologists throughout history. Even with recent scientific investigations of dreaming, dreams still remain something of a mystery. Some experts suggest that dreams represent the replay of the day's events as a critical mechanism in the formation of memories, while others claim that the content of dreams is simply the result of random activity in the brain.

Any of the suitable technologies and materials set forth and incorporated herein may be used to implement various example aspects of the invention as would be apparent to one of skill in the art.

Although exemplary embodiments and applications of the invention have been described herein including as described above and shown in the included example Figures, there is no intention that the invention be limited to these exemplary embodiments and applications or to the manner in which the exemplary embodiments and applications operate or are described herein. Indeed, many variations and modifications to the exemplary embodiments are possible as would be apparent to a person of ordinary skill in the art. The invention may include any device, structure, method, or functionality, as long as the resulting device, system or method falls within the scope of one of the claims that are allowed by the patent office based on this or any related patent application.

The invention claimed is:

1. A mask for treating a patient suffering from obstructive sleep apnea, the mask adapted to be connected to an air flow generator and constructed to cover at least the nostrils of the patient, the mask comprising:
   a cavity in fluid connection with the nostrils of the patient;
   an inlet pressure port constructed to be attached to the air flow generator;
   the inlet pressure port fluidly connected to the cavity via an inlet pressure one-way valve that is constructed to allow air flow from the air flow generator to the cavity with little resistance and block air flow from the cavity to the air flow generator;
   the inlet pressure port fluidly connected to an expiration valve, wherein the expiration valve is fluidly connected to the cavity and to the outside of the mask, the expiration valve restricts air flow from the cavity to the outside of the mask, wherein an opening pressure of the expiration valve is variable and dependent on the pressure of air in the inlet pressure port as follows: (1) the opening pressure of the expiration valve increases when the pressure or air in the inlet pressure port increases; and/or (2) the opening pressure of the expiration valve decreases when the pressure or air in the inlet pressure port decreases; and
   an inspiration one-way valve fluidly connected to the cavity and to the outside of the mask, the inspiration valve is constructed to allow air flow from the outside of the mask into the cavity with little resistance and block air flow from the cavity to the outside of the mask.

2. The mask of claim 1 further comprising a valve cartridge that comprises the inlet pressure one way valve, the expiration valve and the inspiration one way valve.

3. The mask of claim 2, wherein the cartridge is removable.

4. The mask of claim 1 wherein the inspiration one way valve comprises two valves.

5. The mask of claim 1 further comprising an ambient pressure port, wherein the inspiration one-way valve and the expiration valve are fluidly connected to the ambient port.

6. The mask of claim 1, wherein the inlet pressure one way valve comprises a membrane and a valve seat.

7. The mask of claim 6, wherein the shape of the membrane depends on the pressure of air in the inlet pressure port.

8. The mask of claim 1, wherein the inspiration one way valve comprises a membrane and a valve seat.

9. The mask of claim 1, wherein the expiration valve comprises a membrane and a valve seat.

10. The mask of claim 1, wherein the opening pressure of the expiration valve is substantially zero when the pressure of air in the inlet pressure port is substantially zero.

11. A mask for treating a patient suffering from obstructive sleep apnea, the mask adapted to be connected to an air flow generator and constructed to cover at least the nostrils of the patient, the mask comprising:
   a cavity in fluid connection with the nostrils of the patient;
   an inlet pressure port constructed to be attached to the air flow generator;
   the inlet pressure port fluidly connected to the cavity via an inlet pressure one-way valve;
   the inlet pressure port fluidly connected to an expiration valve, wherein the expiration valve is fluidly connected to the cavity and to the outside of the mask, the expiration valve restricts air flow from the cavity to the outside of the mask, wherein an opening pressure of the expiration valve is variable and dependent on the pressure of air in the inlet pressure port as follows: (1) the opening pressure of the expiration valve increases when the pressure or air in the inlet pressure port increases; and/or (2) the opening pressure of the expiration valve decreases when the pressure or air in the inlet pressure port decreases;

an inspiration one-way valve fluidly connected to the cavity and to the outside of the mask;

the mask having at least an inspiration mode, a rest/apnea mode and an expiration mode;

the inspiration mode occurs when the patient inspires air, during which the inspiration one-way valve and the inlet pressure one-way valve are open;

the rest/apnea mode occurs when the patient is neither inspiring air nor expiring air, during which the inlet pressure one-way-valve is open, and the expiration valve and inspiration one-way valve are closed; and the expiration mode occurs when the patient expires air, during which the expiration valve is open and the inlet pressure one-way valve and the inspiration one-way valve are closed.

12. The mask of claim 11, wherein the mask comprises a disconnected mode when the air flow generator is not providing airflow to the mask:

during which when a patient inspires the inspiration one-way valve and the expiration valve are open; and during which when a patient expires the inspiration one-way valve is closed and the expiration valve is open.

13. The mask of claim 11, wherein the mask comprises a disconnected mode when the air flow generator is not providing airflow to the mask:

during which when a patient inspires the inspiration one-way valve is open; and during which when a patient expires the inspiration one-way valve is closed and the expiration valve is open.

14. The mask of claim 11, wherein the opening pressure of the expiration valve is substantially zero when the pressure of air in the inlet pressure port is substantially zero.

15. A system for treating a patient suffering from obstructive sleep apnea, system comprising:

an air flow generator, which further comprises a controller that adjusts an air flow pressure and volume to be generated;

a tube connected to the air flow generator;

a mask constructed to cover at least the nostrils of the patient, the mask comprising:

a cavity in fluid connection with the nostrils of the patient;

an inlet pressure port constructed to be attached to the air flow generator via the tube;

the inlet pressure port fluidly connected to the cavity via an inlet pressure one-way valve that is constructed to allow air flow from the air flow generator to the cavity with little resistance and block air flow from the cavity to the air flow generator;

the inlet pressure port fluidly connected to an expiration valve, wherein the expiration valve is fluidly connected to the cavity and to the outside of the mask, the expiration valve restricts air flow from the cavity to the outside of the mask, wherein an opening pressure of the expiration valve is variable and dependent on the pressure of air in the inlet pressure port as follows: (1) the opening pressure of the expiration valve increases when the pressure or air in the inlet pressure port increases; and/or (2) the opening pressure of the expiration valve decreases when the pressure or air in the inlet pressure port decreases; and an inspiration one-way valve fluidly connected to the cavity and to the outside of the mask, the inspiration valve is constructed to allow air flow from the outside of the mask into the cavity with little resistance and block air flow from the cavity to the outside of the mask.

16. The system of claim 15, wherein the controller comprises a delay circuit that delays the generation of air flow from the air flow generator for a predetermined amount of time.

17. The system of claim 16, wherein a predetermined maximum pressure is set and the air flow generator gradually increases the pressure of air generated until the maximum pressure is reached.

18. The system of claim 17, wherein the sleep detector is worn by the patient and is adapted to take biometric readings of the patient.

19. The system of claim 17, wherein the sleep detector is wirelessly connected to the controller.

20. The system of claim 15, further comprising a sleep detector that signals the controller that the patient is asleep, thus activating the generation of air flow from the air flow generator.

21. The system of claim 20, wherein a predetermined maximum pressure is set and the air flow generator gradually increases the pressure of air generated until the maximum pressure is reached.

22. The system of claim 15, wherein the tube consists of a single lumen connecting the mask to the air flow generator.

23. The system of claim 15, wherein the opening pressure of the expiration valve is substantially zero when the pressure of air in the inlet pressure port is substantially zero.

* * * * *